(12) United States Patent
Yu et al.

(10) Patent No.: US 8,435,783 B2
(45) Date of Patent: *May 7, 2013

(54) PLANT ARTIFICIAL CHROMOSOME PLATFORMS VIA TELOMERE TRUNCATION

(75) Inventors: Weichang Yu, Columbia, MO (US); Juan M. Vega, Madrid (ES); James Birchler, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/206,501

(22) Filed: Aug. 9, 2011

(65) Prior Publication Data

US 2012/0047609 A1 Feb. 23, 2012

Related U.S. Application Data

(63) Continuation of application No. 11/746,558, filed on May 9, 2007, now Pat. No. 7,993, 913.

(60) Provisional application No. 60/798,830, filed on May 9, 2006, provisional application No. 60/862,733, filed on Oct. 24, 2006.

(51) Int. Cl.
| | | |
|---|---|---|
| *C12N 15/82* | (2006.01) | |
| *C12N 15/63* | (2006.01) | |
| *C12N 15/00* | (2006.01) | |
| *C07H 21/04* | (2006.01) | |
| *A01H 5/00* | (2006.01) | |

(52) U.S. Cl.
USPC ........ 435/320.1; 435/468; 435/412; 800/278; 800/295; 800/320.1; 536/23.1; 536/24.1; 536/24.2

(58) Field of Classification Search .................. None
See application file for complete search history.

(56) References Cited

U.S. PATENT DOCUMENTS

| | | | |
|---|---|---|---|
| 5,270,201 | A | 12/1993 | Richards et al. |
| 5,721,118 | A | 2/1998 | Scheffler |
| 6,133,503 | A | 10/2000 | Scheffler |
| 6,716,608 | B1 | 4/2004 | Ishikawa et al. |
| 6,900,012 | B1 | 5/2005 | Preuss et al. |
| 7,015,372 | B2 | 3/2006 | Preuss et al. |
| 2004/0081982 | A1 | 4/2004 | Choo et al. |
| 2009/0165176 | A1 | 6/2009 | Ananiev et al. |

FOREIGN PATENT DOCUMENTS

| | | |
|---|---|---|
| JP | 2003-310263 | 11/2003 |
| WO | WO 01/11020 | 2/2001 |
| WO | WO 02/50288 | 6/2002 |
| WO | WO 2005/010142 | 2/2005 |
| WO | WO 2007/030510 A2 | 3/2007 |

OTHER PUBLICATIONS

Kato et al 2005 Cytogenetic Genome Research 109:156-165, provided in parent application 11746558.*

Adams et al, "Loss and recovery of *Arabidopsis*-type telomere repeat sequences 5' - (TTTAGGG)$_n$ 3' in the evolution of a major radiation of flowering plants," *Proc. R. Soc. Lond. B*, 268:1541-1546, 2001.
Albert et al, "Site-specific integration of DNA into wild-type and mutant *lox* sites placed in the plant genome," *Plant J.*, 7:649-659, 1995.
Alfenito et al, "Molecular characterization of a mazie B chromosome centric sequences," *Genetics*, 135:589-597, 1993.
Barnett et al, "Telomere directed fragmentation of mammalian chromosomes," *Nucleic Acids Research*, 21:27-36, 1993.
Basu et al, "Efficient assembly of de novo human artificial chromosomes from large genomic loci," *BMC Biotechnology*, 5:21, 2005.
Bayne et al, "An analysis of Xq breakpoints created by telomere-associated chromosome fragmentation," *Cytogenet. Cell Genet.*, 64:157, Abstract No. 18, 1993.
Brock et al, "An unstable minichromosome generates variegated *oil yellow maize* seedlings," *Chromosome*, 104:575-583, 1996.
Bunnell et al, "Development of mammalian artificial chromosomes for the treatment of genetic diseases: Sandhoff and Krabbe diseases," *Expert Opin. Biol. Ther.*, 5:195-206, 2005.
Chiurazzi et al, "Termini and telomees in T-DNA transformation," *Plant Mol. Biol.*, 26:923-934, 1994.
Dawe et al. "Induction of centromeric activity in maize by suppressor of meiotic drive 1," *Proc. Natl. Acad. Sci. USA*, 93:8512-8517, 1996.
Farr et al. "Functional reintroduction of human telomeres into mammalian cells," *Proc. Natl. Acad. Sci. USA*, 88:7006-7010, 1991.
Farr et al, "Generation of a human X-derived minichromosome using telomere-associated chromosome fragmentation," *Embo J.*, 14:5444-5454, 1995.
Farr et al . "Telomere-associated chromosome fragmentation: applications in genome manipulation and analysis," *Nat. Genet.*, 2:275-282, 1992.
Guiducci et al, "Use of a human minichromosome as a cloning and expression vector for mammalian cells," *Human Mol. Genetics*, 8:1417-1424, 1999.
Harrington et al, "Formation of *de novo* centromeres and construction of first-generation human artificial microchromosomes," *Nat. Genetics*, 15:345-355, 1997.
Heller et al, "Mini-chromosomes derived from the human Y chromosome by telomere directed chromosome breakage," *Proc. Natl. Acad. Sci. USA*, 93:7125-7130, 1996.
Henning et al, "Human artificial chromosomes generated by modification of a yeast artificial chromosome containing both human alpha satellite and single-copy DNA sequences," *Proc. Natl. Acad. Sci. USA*, 96:592-597, 1999.
Ikeno et al, "Construction of YAC-based mammalian artificial chromosomes," *Nat. Biotechnology*, 16:431-439, 1998.
Itzhaki et al, "Targeted breakage of a human chromosome mediated by cloned human telomeric DNA," *Nat. Gen.*, 2:283-287, 1992.
Jiang et al, "A molecular view of plant centromeres," *Trends in Plant Sci.*, 8:570-575, 2003.
Kamps et al, "RFLP mapping of the maize gametophytic restorer-of-fertility locus (rf3) and aberrant pollen transmission of the nonrestoring rf3 allele," *Theoretical and Applied Genetics*, 95:525-531, 1997.
Kaszás et al, "Meiotic transmission rates correlate with physical features of rearranged centromeres in maize," *Genetics*, 150:1683-1692, 1998.

(Continued)

*Primary Examiner* — Brent T Page
(74) *Attorney, Agent, or Firm* — Dentons US LLP (57) ABSTRACT

The invention provides engineered plant minichromosomes generated by telomere mediated truncation of native chromosomes. These minichromosomes are faithfully transmitted from one generation to the next and provide an ideal platform for breeding genes into desired plant varieties with out problems, such as linkage drag, associated with standard breeding methods.

39 Claims, 2 Drawing Sheets

OTHER PUBLICATIONS

Kato et al, "Minichromosomes derived from the B chromosome of maize," *Cytogenet Genomes Res.*, 109:156-165, 2005.

Katoh et al, "Construction of a novel human artificial chromosome vector for gene delivery," *Biochem. Biophys. Res. Commun.*, 321:280-290, 2004.

Kilburn et al, "Insertion of a telomere repeat sequence into a mammalian gene causes chromosome instability," *Mol. Cell. Biol.*, 21:126-135.

Kistler et al, "Telomere-mediated chromosome breakage," www.fgsc.net/methods/Kistler.html, Oct. 19, 2000.

Maguire, "Meiotic behavior of a tiny fragment chromosome that carries a transposed centromere," *Genome*, 29:744-747, 1987.

McClintock, "The production of homozygous deficient tissues with mutant characteristics by means of the aberrant mitotic behavior of ring-shaped chromosomes," *Genetics*, 23:315-376, 1938.

Mills et al, "Generation of an ~ 2.4 Mb human X centromere-based minichromosome by targeted telomere-associated chromosome fragmentation in DT40," *Hum. Mol. Genet.*, 8:751-761, 1999.

Murray et al, "Construction and behavior of circularly permuted and telocentric chromosomes in *Saccharomyces cerevisiae*," *Mol. Cell Biol.*, 6:3166-3172, 1986.

Murray et al, "Construction of artificial chromosomes in yeast," *Nature*, 305:189-193, 1983.

Nasuda et al, Stable barley chromosomes without centromeric repeats, *Proc. Natl. Acad. Sci. USA*, 102:9842-9847, 2005.

Peacock et al., "Highly repeated DNA sequence limited to knob heterochromatin in maize," *Proc. Nat. Acad. Sci. USA*, 78:4490-4494, 1981.

Raimondi et al, "Gene targeting to the centromeric DNA of a human minichromosome," *Human Gene Therapy*, 7:1103-1109, 1996M.

Richards et al, "Isolation of a higher eukaryotic telomere from *Arabidopsis thaliana*," *Cell*, 53(1): 127-136, 1988.

Rosato et al, "Genome size and numerical polymorphism for the B chromosome in races of maize (*Zea mays* SSP, *Mays*, Poaceae," *Am. J. Botany*, 85:168-174, 1998.

Saffery et al, "Construction of neocentromere-based human minichromosomes by telomere-associated chromosomal truncation,"*Proc. Natl. Acad. Set. USA*, 98:5705-5710, 2001.

Schubert, "Alteration of chromosome numbers by generation of minichromosomes—is there a lower limit of chromosome size for stable segregation?" *Cytogenet Cell Genet.*, 93:175, 2001.

Shen et al, "A structurally defined mini-chromosome vector for the mouse germ line," *Curr. Biol.*, 10:31-34, 2000.

Shen et al, "Human mini-chromosomes in mouse embryonal stem cells," *Hum. Mol. Genet.*, 6:1375-1382, 1997.

Shinohara et al, "Stability of transferred human chromosome fragments in cultured cells and in mice," *Chromosome Res.*, 8:713-725, 2000.

Tomizuka et al, "Double trans-chromosomic mice: maintenance of two individual human chromosome fragments containing Ig heavy and kappa loci and expression of fully human antibodies," *Pro.c Natl. Acad. Sci. USA*, 97:722-727, 2000.

Tomizuka et al, "Functional expression and germlike transmission of a human chromosome fragment in chimaeric mice," *Nat. Genet.*, 16:133-143, 1997.

Voet et al, "Efficient male and female germline transmission of a human chromosomal vector in mice," *Genome Res.*, 11:124-136, 2001.

Willard, "Chromosome manipulation: a systematic approach toward understanding human chromosome structure and function," *Proc. Natl. Acad. Sci., USA*, 93:6847-6850, 1996.

Yamada et al, "Minichromosome formation in *Chlorella* cells irradiated with electron beams," *J. of Bioscience and Bioengineering*, 95:601-607, 2003.

Yamamoto et al, "Retrotransposon-mediated restoration of *Chlorella* telomeres; accumulation of Zepp retrotransposons at termini of newly formed minichromosomes," *Nucleic Acids Research*, 31:4646-4653, 2003.

Yang et al, "Human mini-chromosomes with minimal centromeres," *Human Mol. Genet.*, 9:1891-1902, 2000.

Yu et al, "Characterization of a maize isochromosome 8S•8S," *Genome*, 49:700, 2006.

Yu et al, "Neocentromere-mediated chromosome movement in maize," *J. Cell Biol.*, 139:831-840, 1997.

Zheng et al "Time course study of the chromosome-type breakage-fusion-bridge cycle in maize," *Genetics*, 153:1435-1444, 1999.

PCT International Search Report and Written Opinion issued in International Application No. PCT/US2007/068589, Jun. 11, 2007.

\* cited by examiner

PLANT ARTIFICIAL CHROMOSOME PLATFORMS VIA TELOMERE TRUNCATION

This application is a continuation of U.S. patent application Ser. No. 11/746,558 filed May 9, 2007, now U.S. Pat. No. 7,993,913, that claims the priority of U.S. Provisional Patent Application Ser. No. 60/798,830, filed May 9, 2006, and of U.S. Provisional Patent Application Ser. No. 60/862,733, filed Oct. 24, 2006, the entire disclosures of which are specifically incorporated herein by reference in their entireties.

BACKGROUND OF THE INVENTION

1. Field of the Invention

The invention relates to the fields of molecular biology and plant genetics. More specifically, the invention relates to plant artificial minichromosome platforms and methods for their production and use.

2. Description of Related Art

Maintenance and inheritance of chromosomes in an organism typically requires three essential elements: origins of replication, a centromere and telomeres, as previously identified with yeast artificial chromosomes. Murray and Szostak (1983) for example described a cloning system based on the in vitro construction of linear yeast artificial chromosomes. However, none of the nucleic acid elements that were identified are sufficient to maintain artificial chromosomes in multicellular eukaryotic systems.

One method for generating an artificial chromosome is by de novo construction, i.e., assembly of centromeres, telomeres and selectable markers and reintroduction into plants (U.S. Pat. No. 7,015,372). However, chromosomes are known to have a minimal size limit for efficient transmission through meiosis (Schubert, 2001). Although most de novo mammalian minichromosomes can transmit during mitosis, the transmission of such minichromosomes in germlines has not been reported. The only meiotically transmitted de novo artificial chromosomes in eukaryotes to date are yeast artificial chromosomes (Murray and Szostak, 1983; Murray and Szostak, 1986). Additionally, it has been indicated that plant centromeres need to be greater than about one megabase in size for normal transmission (Kaszas and Birchler, 1998) and this size is larger than can currently be assembled in vitro.

In contrast, some truncated chromosomes with native centromeres are transmissible through meiosis (Shinohara et al., 2000; Tomizuka et al., 1997, 2000; Voet et al., 2001; Shen et al., 1997, 2000; Schubert, 2001; Zheng et al., 1999; Kato et al., 2005; McClintock, 1938; Brock and Pryor, 1996; Nasuda et al., 2005). One method for truncating chromosomes that has been applied in mammalian systems is telomere mediated truncation (Farr et al., 1991, 1992, 1995; Barnett et al., 1993; Itzhaki et al., 1992; Heller et al., 1996; Mills et al., 1999; Saffery et al., 2001). However, no method for telomere mediated truncation of plant chromosomes has been described to date.

Other methods of chromosome deletion have been applied to plant systems. For example, altered maize chromosomes have been generated by X-ray or gamma irradiation of maize pollen (McClintock, 1938; Brock and Pryor, 1996) or through a B-9 translocation with duplicated 9S (Zheng et al., 1999; Kato et al., 2005). However, altered chromosomes created by these methods have lacked stable transmission during meiosis or mitosis, do not carry site specific recombination sites, have not enabled efficient expression of heterologous sequences or have been difficult to produce. Thus, there remains a great need in the art for methods of producing and using plant minichromosomes.

SUMMARY OF THE INVENTION

The invention overcomes limitations in the art by providing plant minichromosomes that can be efficiently transmitted through mitosis and meiosis. The term "minichromosome" refers to engineered chromosomes made by deleting portions of a native chromosome. Thus, minichromosomes are distinct from artificial chromosomes made de novo by recombinant DNA techniques. In specific embodiments, plant minichromosomes described herein are provided derived from a starting, native plant chromosome that is truncated by the insertion of telomere repeats. Thus, plant minichromosomes of the invention may be defined as comprising at least one chromosome arm that has been truncated. In some further embodiments, a plant minichromosome is truncated in both arms. A plant minichromosomes may, in some aspects, be efficiently transmitted during mitosis and meiosis in a plant that is the same species as the plant of the starting chromosome. It will be understood by one of skill in the art that such minichromosomes generally comprise a functional centromere and origins of replication, both of which allow faithful maintenance.

In one aspect of the invention, a plant minichromosome comprises a native centromere. Native centromeres are found on endogenous chromosomes and are comprised of centromere repeats (Jiang et al., 2003). These sequences provide for efficient segregation of chromosomes during cell division such as mitosis and meiosis. Thus, in certain aspects of the invention a plant minichromosome is defined as comprising a native plant centromere sequence. In further embodiments a minichromosome of the invention may be defined as not comprising a neocentromere.

A minichromosome may further comprise engineered telomere sequences. As used herein the term "engineered telomere sequence" refers to telomere sequence that are in a different context than those found in a native chromosome. For example, engineered telomere sequences may be in a different position relative to the centromere than telomeres found in a native chromosome. In particular, engineered telomere sequences in minichromosomes of the invention may be closer to the centromere of the minichromosome as compared to a native telomere. For example, in a plant minichromosome of the invention, an engineered telomere sequence may be defined as about 10 kb to about 10 Mb from the centromere of the native chromosome sequence. In more specific embodiments, an engineered telomere may be about 10 kb to about 5 Mb or about 100 kb to about 1, 2, 3, 4, or 5 Mb from the centromere of a native chromosome sequences. Plant minichromosomes of the invention may further comprise two engineered telomere sequences, which may be different distances from the centromere of the minichromosome.

Engineered telomere sequences may be from a variety of sources. For example, engineered telomere sequences may be from the same plant species or variety as the native chromosome sequences or from a different plant species relative to the native chromosome sequences. For example, telomere sequences may be the cloned telomere sequences from pAtT4 comprising direct repeats of the *Arabidopsis*-type telomeric motif, TTTAGGG (SEQ ID NO:1), or derivatives thereof (Richards and Ausubel, 1988). In this case each repeat comprises 430 base pairs of telomeric sequence. Engineered telomere repeat sequences may be from maize, wheat, oats, rice, *Arabidopsis* or soybean. It will be understood by the skilled artisan that engineered telomeres may comprise a plurality of telomere repeat sequences. For example, in certain embodiments an engineered telomere of the invention may comprise between 2 and 100, 2 and 50 or 2 and 10 repeats, including 6 repeats. In some embodiments of the invention, telomere sequences in a telomere truncation vector such as those exemplified herein (e.g., pWY76, pWY86 and pJV21) are provided. In one embodiment of the invention, a telomere truncation vector may be employed to generate a truncated minichromosome. The telomere truncation vector may be comprised on the minichromosome or may be separate from it. In one embodiment of the invention, the telomere truncation vector may become deleted during the generation of the minichromosome. A transgene could then, for example, be introduced into the minichromosome to generate a minichromosome comprising one or more added transgene(s). A minichromosome formed by such methods comprises one embodiment of the invention.

One aspect of plant minichromosomes is their size. Minichromosomes described herein preferably encode a minimal number of endogenous genes that may deleteriously affect the phenotype of a plant comprising the minichromosome. Thus, it may be preferred that a large portion of an endogenous chromosome be deleted to make a minichromosome, while maintaining a sufficient size for stable transmission. This may be important when the native chromosome is an A chromosome. B chromosomes do not typically encode essential functions and therefore may be less likely to create deleterious phenotypes. Nonetheless, it has also been observed that minichromosomes that are too small are not faithfully maintained through mitosis and meiosis. Thus, in certain embodiments of the invention, a plant minichromosome comprises a native plant chromosome sequence wherein about 1 to about 99.9 percent of the native chromosome sequence is deleted. In some embodiments, about 10, 20, 25, 35, 50, 75, 85, 90, 93, 95, 97, 99, 99.5 or 99.9 percent or any range derivable therein of the native chromosome sequence is deleted in a minichromosome.

In certain further aspects of the invention, a plant minichromosome may be defined by its size. For example, a plant minichromosome may be defined as about 0.1 to about 20 or 30 Mb in size. In further embodiments, a plant minichromosome may be about 1, 1.5, 2, 2.5, 3, 4, 5, 7.0, 9, 10, 20, 50 or 100 Mb in size or any ranger derivable therein. For instance, in some instances plant minichromosomes described herein are between about 1 and 10 Mb or between about 5 and 10 Mb in size.

In some aspects of the invention, a plant minichromosome may be defined as being transmitted through mitosis with a 100% frequency. In further cases, a plant chromosome is defined by the frequency with which it is transmitted during meiosis. For instance, a plant minichromosome may be transmitted with greater than about a 10%, 20%, 25% or 30% frequency during meiosis (50% being perfect transmission). Thus, a plant chromosome of the invention may comprise a truncated A or B chromosome that is transmitted with greater than 35% frequency during meiosis when the minichromosome is transmitted in a plant of the same species as the starting chromosome.

A variety of plants may be used to make plant minichromosomes according to the invention. In some embodiments, the plant is defined as a dicot or monocot plant. For example, the plant may be alfalfa, *Tripsacum*, corn, canola, rice, soybean, tobacco, turfgrass, oat, rye, *Arabidopsis* or wheat. In certain aspects of the invention, the minichromosome may be defined as from a maize plant.

In further embodiments, a plant minichromosome of the invention may be derived from a plant A chromosome. For example, the minichromosome may comprise native chromosome sequences from an A chromosome e.g., in the case of a maize minichromosome it may comprise native sequences from maize chromosome 1, 2, 3, 4, 5, 6, 7, 8, 9, or 10. In one embodiment a plant minichromosome of the invention is derived from a maize chromosome 7.

In still further embodiments, a plant minichromosome of the invention comprises native chromosome sequences of a plant B chromosome. For certain applications telomere truncated B chromosomes may provide benefit as they comprise non-essential genes that are not expected to interfere with plant phenotype or with expression of transgenes from the chromosome. The telomere truncation methods described herein result in deletion of native chromosomal sequences from the B chromosome, particularly those regions that are distal from the centromere. By deletion of regions of the B chromosome that control non-disjunction through telomere truncation, minichromosomes based on B chromosomes will segregate normally. Virtually any type of plant B chromosomes may be used as described herein to make a plant minichromosomes. For example, a plant minichromosome may comprise native B chromosome sequences from maize, rye or sorghum or from any other plant species with B chromosomes or any species comprising a B chromosome that has been introduced (Jones and Rees, 1982). In some embodiments, chromosomal truncation may be carried out in a plant cell comprising multiple B chromosomes, such as a cell comprising at least 2, 3, 4, 5, 6, 7, 8, 9, 10, 11 or more B chromosomes copies.

In certain aspects of the invention, it may be preferred that a minichromosome comprising plant lacks B chromosomes as presence of an intact B chromosome may cause non-disjunction of B chromosome derived minichromosomes. Thus, in some embodiments, the invention provides a method for manipulating the dosage of a plant minichromosome comprising B chromosomes sequences by introduction of an intact B chromosome or a portion of a B chromosome. For example, the dosage of a plant minichromosome may be modulated by introducing B chromosome sequence that controls B centromere nondisjunction.

A plant minichromosome according to the invention may comprise a selectable marker which confers a growth advantage under particular conditions to plant cells carrying the marker, thereby allowing identification of plants, plants cells or plant parts comprising the minichromosome. A selectable marker may function in bacterial cells. A minichromosome may also comprise "negative" selectable markers which confer susceptibility to an antibiotic, herbicide or other agent, thereby allowing for selection against plants, plant cells or cells of any other organism of interest comprising the particular minichromosome. Furthermore, in some aspects, a plant minichromosome may comprise a male fertility restoration gene such as a Rf3 gene.

A plant minichromosome may further comprise site-specific recombination sequences. For example, minichromosomes of the invention may comprise a lox or FRT site. Site-specific recombination provides a convenient method for moving genes in and out of artificial chromosomes such as the plant minichromosomes of the invention. Random mutagenesis can also be provided in this manner. Methods for using site-specific recombination to mediate in vivo gene transfer are well known in the art. Site-specific recombination may be used to sequentially add genes to a minichromosome in order to provide the genes for an entire biochemical pathway or a set of agronomically elite characteristics. In some aspects of the invention telomere sequence inserted into a starting plant chromosome comprise a site specific recombination sequences. In this aspect plant minichromosomes comprising site specific recombination sequences may be rapidly generated.

In certain further embodiments, a plant minichromosome may comprise genes which control the copy number of the minichromosome within a cell. One example of such a gene is the element of B chromosomes that mediates non-disjunction as described above. One or more structural genes may also be comprised within a minichromosome. Specifically contemplated as being useful are as many structural genes as may be inserted into a minichromosome while still maintaining a functional and faithfully transmitted artificial chromosome. This may include one, two, three, four, five, six, seven, eight, nine or more structural genes.

In another embodiment, the invention provides methods for expressing one or more foreign genes in plants, plant cells or cells of any other organism of interest. The foreign gene(s) may be from any organism, including plants, animals and bacteria. In one embodiment, foreign gene(s) confer improved agronomic characteristics to a given plant. For example, the transgene may confer a trait such as insect resistance, herbicide tolerance, altered carbohydrate metabolism, altered fatty acid metabolism, disease resistance, and pest resistance. It is further contemplated that minichromosomes may be used to simultaneously transfer multiple foreign genes to a plant comprising entire biochemical or regulatory pathways. In yet another embodiment, it is contemplated that the plant minichromosomes can be used as DNA cloning vectors. Such a vector could be used in plant and animal sequencing projects. In some specific cases, a transgene may be introduced into a starting chromosome along with telomere repeat sequences thereby generating a plant minichromosome comprising the transgene.

In a further embodiment there is provided a plant cell comprising the a plant minichromosome. The plant cell may be the same species as the species of the starting plant chromosome, however in certain cases it may be a different species. Thus, a plant or a plant seed comprising a plant minichromosome also forms part of the invention. In certain aspects a plant comprising the minichromosome is a maize plant.

In general methods and compositions of the invention involve telomere mediated chromosome truncation. For example, a vector comprising plant telomeres is introduced into a plant cell. Such vectors may be introduced into a plant cell by any of the methods that are well known in the art, for example DNA bombardment or *Agrobacterium* mediated transformation. For example, in certain embodiments, *Agrobacterium* mediated transformation may be used to generate plant minichromosomes derived from A chromosomes. Conversely, in some case DNA bombardment may be used to generate plant minichromosomes derived from B chromosomes. Upon integration of the telomere sequences into one or more positions of a plant chromosome the chromosome will be truncated at the point of integration. Thus, a method of the invention may comprise transforming a starting plant chromosome with a heterologous nucleic acid comprising at least two telomere repeat sequences and allowing truncation of the starting plant chromosome to occur to produce a plant minichromosome. One or both arms of a chromosome may be truncated by telomere integration. Resultant plant minichromosomes may then be screened to determine their size and origin, for example by Southern blot or FISH.

In some further methods of the invention, a starting plant chromosome is transformed with heterologous nucleic acid sequence comprising telomere repeats and additional sequences such as site specific recombination sequences a transgene or other selected sequence. Alternatively, a starting plant chromosome may be transformed with heterologous nucleic acid sequence comprising telomere repeats to generate a plant minichromosome. Subsequently, the plant minichromosome may be transformed with a second heterologous nucleic acid sequence comprising an additional sequence such as a transgene. For example, additional sequences may comprise an FRT or lox site. In some cases, additional sequence may also comprise a gene that confers insect resistance, herbicide tolerance, altered carbohydrate metabolism, altered fatty acid metabolism, disease resistance, male fertility restoration or pest resistance. Thus, in certain embodiments, the additional gene may be a male fertility restoration gene such as an Rf3 gene. This aspect of the invention may be particularly advantageous since plant minichromosomes that restore male fertility may be transmitted to progeny cells with very high efficiency.

Embodiments discussed in the context of a methods and/or composition of the invention may be employed with respect to any other method or composition described herein. Thus, an embodiment pertaining to one method or composition may be applied to other methods and compositions of the invention as well.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein.

FIG. 1: Examples of chromosomal truncation constructs. Constructs pWY76 and pWY86, and the control construct pWY96 are diagrammed. The meaning of the letter designations in the figure are as follows: LB, T-DNA left border; RB, T-DNA right border; Tvsp, terminator from soybean vegetative storage protein gene; Bar, bialaphos resistance gene as a selectable marker gene; TEV, tobacco etch virus 5' untranslated region; P35S, 2X35S promoter from cauliflower mosaic virus (CaMV); Tnos, Nos terminator from *Agrobacterium tumefaciens*; Tmas, Mas terminator from *A. tumefaciens*;

Pnos, Nos promoter from *A. tumefaciens*; Pmas1', Mas promoter from *A. tumefaciens*; lox and FRT, site-specific recombination sites; HPT, hygromycin B resistance gene; GFP, green fluorescent protein gene; DsRed, red fluorescent protein; FLP, site specific recombinase gene; Telomeres, telomere units of pAtT4 isolated from *Arabidopsis thaliana* (Richards and Ausubel 1988). The arrows indicate the direction of transcription or in the case of the telomere repeats, the chromosomal orientation.

FIG. 2: Structure of pJV21. The four functional parts are indicated by brackets and labeled. LB, left border; RB, right border; lox, lox66 site; Cre, Cre recombinase gene; bar, bialaphos resistance gene; 35S, CaMV 35S promoter; ubi, maize ubiquitin promoter; n3', terminator sequence of the nopaline synthase gene; telo, 400 bp telomere repeats from *Arabidopsis*; NotI and AscI, restriction enzyme sites.

DETAILED DESCRIPTION OF THE INVENTION

One of the goals of plant breeding is the selection of desirable characteristics such as disease and insect resistance, rate of growth, nutrient requirements and yield. Unfortunately, in many plant species different varieties are optimal for geographic and climactic regions. However, breeding a desirable characteristic or gene into each variety can take years since any given characteristic must be selected for while maintaining the specific advantages of a given variety. Modifying some traits or stacking of traits can also require multiple transgenes, which complicates introgression. Thus, ideally genes that impart agronomically superior characteristics could be provided on a separate chromosome and thus would be unlinked to other genes and easily selected in progeny plants. However, until now a plant minichromosome that is capable of encoding genes had not been described.

The invention overcomes limitations in the art by providing plant minichromosomes that may be used to incorporate desirable transgenes. In certain cases, the minichromosome can be introgressed into any particular variety of plant since it will not be linked to any background genes, encoded on other chromosomes. These minichromosomes may further comprise site specific recombination sites that enable genes to be quickly moved in or out of any plant variety comprising the minichromosome. Thus, these new plant minichromosomes reduce the problems associated with linkage drag by providing a genetically isolated expression platform.

I. Recombination Systems

In certain embodiments of the invention plant minichromosomes comprise at least one site specific recombinase site. Site-specific integrase recombinase systems have been identified in several organisms including, but not limited to, the Cre/lox system of bacteriophage P1 (Abremski et al., 1983; U.S. Pat. Nos. 4,959,317; 5,658,772), the FLP/FRT system of yeast (Golic and Lindquist, 1989), the Pin recombinase of *E. coli* (Enomoto et al., 1983), the Gin/gix recombinase of phage Mu (Maeser et al., 1991), the R/RS system of the pSR1 plasmid from *Zygosaccharomyces rouxii* (Onouchi et al., 1991; Araki et al., 1992) and the R recombinase from *Zygosaccharomyces rouxii* (Onouchi et al., 1995). All of these systems have been shown to function in plants (O'Gorman et al., 1991; Maeser et al., 1991; Onouchi et al., 1991; Dale and Ow, 1991). It is believed that site-directed integration systems like Cre/lox or FLP/FRT require a circular DNA intermediate. Of these systems, Cre/lox and FLP/FRT have been widely utilized.

The FLP/FRT system is native to the yeast *Saccharomyces cerevisiae* (Golic and Lindquist, 1989; reviewed in Futcher, 1988). In yeast, the recombinase enzyme (FLP) resides on a 2µ plasmid and recognizes 599 base pair (bp) inverted repeats (FRT) as target sites. The minimal functional sequence unit within the 599 bp repeats includes only 34 bp; two 13 bp inverted repeats separated by an asymmetric 8 bp spacer region although a third, non-essential repeat of the 13 bp sequence is often present (Sauer, 1994). FLP-mediated rearrangement of DNA flanked by inverted repeats of FRT sequence often results in the inversion of the DNA between the FRT target sites. In this case, both FRT sites are retained. FLP recombinase can also recognize directly repeated FRT target sites. FLP-mediated rearrangements of DNA flanked by directly repeated FRT sites often results in the excision of the DNA located between the FRT target sites. In this case, the excised DNA is released in circular form comprising one FRT site while the second FRT site remains on the template DNA molecule. FLP recombinase can also mediate recombination between FRT sites on different DNA molecules; for example, FLP recombinase can mediate recombination between FRT sites on different chromosomes. Sadowski (1995) has shown that recombination catalyzed by FLP/FRT is reversible in nature.

The DNA exchange catalyzed by FLP/FRT can be carried out in vitro as purified FLP recombinase has been shown to mediate recombination between FRT sites (Meyer-Leon et al., 1984). The yeast FLP/FRT combination has also been used to direct site-specific recombination, both excision and amplification of sequences flanked by FRT sites, in *Escherichia coli* (Cox, 1983) as well as in *Drosophila* genomes (Golic and Lindquist, 1989; Golic, 1994). FLP/FRT has also been employed to direct site-specific excision of parts of transgenes from plasmid DNA in maize and rice protoplasts by homologous recombination (see, for example, U.S. Pat. No. 5,527,695). FLP/FRT has also been utilized in stably transformed maize for site-directed excision of sequences inserted into the maize genome which are flanked by FRT sites (U.S. Pat. Nos. 5,929,301 and 6,175,058). Site-specific chromosomal targeting of foreign DNA into bacterial and mammalian chromosomes can also be effected by FLP/FRT (Huang et al., 1991; O'Gorman et al., 1991) and this insertion by FLP into FRT sites has been shown to be reversible in non-yeast genomes (Huang et al., 1997). It is possible to sufficiently alter FRT sites such that recombination occurs but is not reversible (U.S. Pat. No. 6,187,994) or favors a forward reaction relative to a reverse reaction (Senecoff et al., 1988).

A second well characterized recombination system is that of Cre/lox from bacteriophage P1 (Abremski et al., 1983; reviewed in Craig, 1988; Sauer, 1994; Ow, 1996). Cre recombinase (causing recombination) recognizes lox (locus of crossing over (x)) target sequences and mediates site-specific recombination between compatible lox sites. Compatible sites may or may not comprise identical sequences. Lox sites are 34 base pairs in length, comprising two 13 bp inverted repeats separated by 8 bp of other spacer nucleotides. Lox sequences include loxP from bacteriophage P1 (Albert et al., 1995) as well as loxB, loxL, and loxR sites which are nucleotide sequences isolated from *E. coli* (Hoess et al., 1982). Functional variants of loxP sites reported include, but are not limited to lox66, lox71, and lox72 (Albert et al., 1995; Langer et al., 2002). Lox sequences can also be produced by a variety of synthetic techniques which are known in the art. Examples of synthetic techniques for producing functional lox sites are disclosed by Ogilvie et al. (1981) and Ito et al. (1982).

The lox site is an asymmetrical nucleotide sequence and as such, lox sites on the same DNA molecule can have the same or opposite orientation with respect to each other. Recombination between lox sites in the same orientation results in a deletion of the DNA segment located between the two lox sites. In this case, ligation between the resulting ends of the original DNA molecule occurs and a lox site is retained. The deleted DNA segment forms a circular molecule of DNA which also contains a single lox site. Recombination between lox sites in opposite orientations on the same DNA molecule results in an inversion of the nucleotide sequence of the DNA segment located between the two lox sites. In addition, reciprocal exchange of DNA segments proximate to lox sites located on two different DNA molecules can occur. All of these recombination events are catalyzed by the product of the Cre coding region and are reversible. It is possible, however, to sufficiently alter lox sites such that recombination events occur but are resistant to the reverse recombination reaction (Albert et al., 1995; Araki et al., 1997; PCT Publication WO 01/11058) or such that two sites are "non-compatible" recombination substrates for the recombinase (Hoess et al., 1986; Trinh and Morrison, 2000; Lee and Saito, 1988; EP 1 035 208). It is also possible to prevent the reverse reaction from occurring be removing the source of recombinase, for example, by breeding or use of particular regulatory promoters.

Cre recombinase also effects site-directed integration. For example, a lacZ reporter gene was integrated into the genome of Chinese Hamster Ovary (CHO) cells using Cre-recombinase, a single lox site on the lacZ targeting vector and a single lox site previously located within the CHO genomic DNA (Fukushige and Sauer, 1992). Cre recombinase has been shown to mediate recombination between lox sites in yeast (Sauer, 1987) and plants, such as tobacco and *Arabidopsis* (see, for example, U.S. Pat. No. 5,658,772; Medberry, et al., 1995; Albert et al., 1995) as well as in mammalian cells such as mice (Sauer and Henderson, 1988; Fukushige and Sauer, 1992; Sauer, 1998). Site-specific integration of large BAC (bacterial minichromosome) fragments into plant and fungal genomes utilizing a Cre/lox recombination system has also been reported (Choi et al., 2000). It is believed that in order to achieve site-directed integration into a single genomic lox site, a circular DNA molecule comprising a single lox site must be introduced into the cell. Therefore, the methods of the present invention make it possible to achieve site-directed integration of DNA molecules lacking ancillary sequences that are often present in order to replicate and maintain the circular molecules in a bacterial host cell. Wallace et al., (2000) and Day et al., (2000) discuss the use of site-directed integration as a method to pre-select sites in the genome for repeatable expression of transgenes in embryonic stem cells or tobacco, respectively.

Cre recombinase can contact and effect recombination utilizing a number of lox sites including, but not limited to loxP and a number of variants of the wild type loxP site such as lox66 (Albert et al., 1995). The DNA exchange directed by the lox sites occurs in the 8 bp spacer region and essentially effects an exchange of the 13 bp inverted repeats of the two lox sites involved. For example, site-directed recombination in which a single lox site on one DNA molecule recombines with a second single lox site on a second DNA molecule generates a sequence in which the integrated DNA is flanked by a lox site on either side. When the single lox sites on the separate molecules involved are identical, the two resultant lox sites adjacent to the inserted DNA are also identical. If, however, the two single lox sites on the starting molecules are non-identical in the 13 bp inverted repeats, the two resultant lox sites adjacent to the inserted DNA will differ from the starting lox sites. For example, if a first single lox66 site is involved in site-directed integration with a second single lox71 site, the resultant lox sites flanking the inserted DNA comprise sequences of loxP and lox72 sites (Albert et al., 1995).

Site-directed integration utilizing identical lox or FRT sites on the two recombining molecules results in the inserted DNA being flanked by identical recombination sites, a reaction that is easily reversed by the recombinase. To prevent the deletion of the inserted sequence, it is often desirable to remove the source of recombinase enzyme, for example, by segregation or by placing the recombinase gene under the control of an inducible promoter and removing the inducing source. Alternatively, one of skill in the art may use site-specific recombination sequences designed such that after the integration reaction, the resultant sites are non-compatible for a reverse reaction or recombine at a reduced rate.

One of skill in the art will recognize that the integrase enzyme, such as Cre or FLP recombinase, can be provided to the target site or sites, such as lox or FRT, by any means known in the art. For example, the recombinase can be transiently supplied by expression from a gene, and appropriate control sequences, that reside on a separately maintained plasmid within the host cells. The recombinase gene and appropriate control sequences can be inserted into the genome of the organism and stably expressed in the host cells. Alternatively, sexual crossing or breeding may be used to introduce the recombinase to cells containing the target lox or FRT site or sites; in this instance, an organism such as plant containing the recombinase gene could be crossed to a plant containing the target lox or FRT sites and progeny from this union would contain both the recombinase and the target site or sites. In some cases, mRNA coding for the desired recombinase can be introduced into the host cells to encode and provide the recombinase protein. In other cases, one may introduce isolated recombinase protein into a host cell comprising a target recombination site. In any of these cases, the promoter directing recombinase expression may be, but not limited to, constitutive or inducible in manner. One of skill in the art will also recognize that the genes for recombinase genes such as Cre or FLP may be isolated from bacteriophage P1 or *Saccharomyces cerevisiae*, respectively, and utilized directly in a new host system or the gene sequence may be optimized for codon usage for expression in the transgenic host. In a similar fashion, one of skill in the art will recognize that natively occurring as well as synthetic target sites may be recognized and mediate recombination with an appropriate recombinase.

Examples of recombinase mediated gene replacement or gene excision typically utilize two target sites flanking the sequence to be replaced or excised. For example, Odell et al. (U.S. Pat. No. 5,658,772) disclose the use of two loxP sites and Cre-recombinase to generate specific gene replacements in tobacco. The Cre/lox system has also been used in an inducible manner to activate and to remove transgenes in transgenic plants (PCT Publication WO 01/40492). Baszczynski et al. (U.S. Pat. No. 6,187,994) disclose the use of multiple, non-identical FRT sites and FLP-recombinase to generate a variety of gene alterations in maize. Baszczynski et al. (U.S. Pat. No. 6,262,341) also disclose the use of a chimeric Cre/FLP recombinase with dual target site specificity to effect recombination of DNA sequences flanked by a lox sequence on one side and a FRT sequence on another side. In each of these cases, the integration or excision of sequences generates extraneous DNA fragments as part of the recombination schema. Site-directed integration, however, may utilize only one target site in the recipient genome. The present invention proposes Cre-mediated, targeted integration of a non-replicating, in vitro generated, transformation-ready circular molecule containing a first single lox site into a second single lox site previously introduced into the target genome.

II. Genes for Use in the Invention

It will be understood by one of skill in the art that minichromosomes of the instant invention may be used to express a variety of genes. In some preferred embodiments such genes confer agronomically elite characteristics to a plant comprising a minichromosome of the invention. Some none limiting examples of genes for use in the instant invention are provided below.

A. Herbicide Resistance

Numerous herbicide resistance genes are known and may be employed with the invention. An example is a gene conferring resistance to a herbicide that inhibits the growing point or meristem, such as an imidazalinone or a sulfonylurea. Exemplary genes in this category code for mutant ALS and AHAS enzyme as described, for example, by Lee et al., (1988); Gleen et al., (1992); and Miki et al., (1990).

Resistance genes for glyphosate (resistance conferred by mutant 5-enolpyruvl-3 phosphoshikimate synthase (EPSP) and aroA genes, respectively) and other phosphono compounds such as glufosinate (phosphinothricin acetyl transferase (PAT) and Streptomyces hygroscopicus phosphinothricin-acetyl transferase (bar) genes) may also be used. See, for example, U.S. Pat. No. 4,940,835 to Shah, et al., which discloses the nucleotide sequence of a form of EPSPS which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a phosphinothricin-acetyltransferase gene is provided in European application No. 0 242 246 to Leemans et al. DeGreef et al., (1989), describe the production of transgenic plants that express chimeric bar genes coding for phosphinothricin acetyl transferase activity. Exemplary of genes conferring resistance to phenoxy propionic acids and cyclohexanediones, such as sethoxydim and haloxyfop are the Acct-S1, Accl-S2 and Acct-S3 genes described by Marshall et al., (1992).

Genes are also known conferring resistance to a herbicide that inhibits photosynthesis, such as a triazine (psbA and gs+ genes) and a benzonitrile (nitrilase gene). Przibilla et al., (1991), describe the transformation of Chlamydomonas with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., (1992).

B. Male Sterility and Restoration of Male Fertility

Examples of genes conferring male sterility as well as restorers of male fertility are known in the art and include those disclosed in U.S. Pat. Nos. 3,861,709, 3,710,511, 4,654, 465, 4,727,219, 5,530,191, 5,625,132, and 5,689,041, each of the disclosures of which are specifically incorporated herein by reference in their entirety.

Male sterility genes can increase the efficiency with which hybrids are made, in that they eliminate the need to physically emasculate the corn plant used as a female in a given cross.

Where one desires to employ male-sterility systems with a corn plant in accordance with the invention, it may be beneficial to also utilize one or more male-fertility restorer genes.

For example, where cytoplasmic male sterility (CMS) is used, hybrid seed production requires three inbred lines: (1) a cytoplasmically male-sterile line having a CMS cytoplasm; (2) a fertile inbred with normal cytoplasm, which is isogenic with the CMS line for nuclear genes ("maintainer line"); and (3) a distinct, fertile inbred with normal cytoplasm, carrying a fertility restoring gene ("restorer" line). The CMS line is propagated by pollination with the maintainer line, with all of the progeny being male sterile, as the CMS cytoplasm is derived from the female parent. These male sterile plants can then be efficiently employed as the female parent in hybrid crosses with the restorer line, without the need for physical emasculation of the male reproductive parts of the female parent.

The presence of a male-fertility restorer gene results in the production of fully fertile $F_1$ hybrid progeny. If no restorer gene is present in the male parent, male-sterile hybrids are obtained. Such hybrids are useful where the vegetative tissue of the corn plant is utilized, e.g., for silage, but in most cases, the seeds will be deemed the most valuable portion of the crop, so fertility of the hybrids in these crops must be restored. Therefore, one aspect of the current invention concerns the hybrid corn plant CH389090 comprising a genetic locus capable of restoring male fertility in an otherwise male-sterile plant. Examples of male-sterility genes and corresponding restorers which could be employed with the plants of the invention are well known to those of skill in the art of plant breeding and are disclosed in, for instance, U.S. Pat. Nos. 5,530,191; 5,689,041; 5,741,684; and 5,684,242, the disclosures of which are each specifically incorporated herein by reference in their entirety. For example, restorer gene may be an Rf3 gene (Duvick, 1965; Chase and Gabay-Laughnan 2004; Gabay-Laughnan et al., 2004) or genes used in the Barnase/Barstar restoration system (Mariani et al., 1990; Mariani et al., 1992)

C. Disease Resistance

Plant defenses are often activated by specific interaction between the product of a disease resistance gene (R) in the plant and the product of a corresponding avirulence (Avr) gene in the pathogen. A plant line can be transformed with cloned resistance gene to engineer plants that are resistant to specific pathogen strains. See, for example Jones et al., (1994) (cloning of the tomato Cf-9 gene for resistance to Cladosporium falvum); Martin et al., (1993) (tomato Pto gene for resistance to Pseudomonas syringae pv.); and Mindrinos et al., (1994) (Arabidopsis RSP2 gene for resistance to Pseudomonas syringae).

A viral-invasive protein or a complex toxin derived therefrom may also be used for viral disease resistance. For example, the accumulation of viral coat proteins in transformed plant cells imparts resistance to viral infection and/or disease development effected by the virus from which the coat protein gene is derived, as well as by related viruses. See Beachy et al., (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus.

A virus-specific antibody may also be used. See, for example, Tavladoraki et al., (1993), who show that transgenic plants expressing recombinant antibody genes are protected from virus attack.

Logemann et al., (1992), for example, disclose transgenic plants expressing a barley ribosome-inactivating gene have an increased resistance to fungal disease.

D. Waxy Starch

The waxy characteristic is an example of a recessive trait. In this example, the progeny resulting from the first backcross generation (BC1) must be grown and selfed. A test is then run on the selfed seed from the BC1 plant to determine which BC1 plants carried the recessive gene for the waxy trait. In other recessive traits additional progeny testing, for example growing additional generations such as the BC1S1, may be required to determine which plants carry the recessive gene.

E. Insect Resistance

One example of an insect resistance gene includes a *Bacillus thuringiensis* protein, a derivative thereof or a synthetic polypeptide modeled thereon. See, for example, Geiser et al., (1986), who disclose the cloning and nucleotide sequence of a Bt δ-endotoxin gene. Moreover, DNA molecules encoding δ-endotoxin genes can be purchased from the American Type Culture Collection, Manassas, Va., for example, under ATCC Accession Nos. 40098, 67136, 31995 and 31998. Another example is a lectin. See, for example, Van Damme et al., (1994), who disclose the nucleotide sequences of several *Clivia miniata* mannose-binding lectin genes. A vitamin-binding protein may also be used, such as avidin. See PCT application US93/06487, the contents of which are hereby incorporated by reference. This application teaches the use of avidin and avidin homologues as larvicides against insect pests.

Yet another insect resistance gene is an enzyme inhibitor, for example, a protease or proteinase inhibitor or an amylase inhibitor. See, for example, Abe et al., (1987) (nucleotide sequence of rice cysteine proteinase inhibitor), Huub et al., (1993) (nucleotide sequence of cDNA encoding tobacco proteinase inhibitor I), and Sumitani et al., (1993) (nucleotide sequence of *Streptomyces nitrosporeus* α-amylase inhibitor). An insect-specific hormone or pheromone may also be used. See, for example, the disclosure by Hammock et al., (1990), of baculovirus expression of cloned juvenile hormone esterase, an inactivator of juvenile hormone.

Still other examples include an insect-specific antibody or an immunotoxin derived therefrom and a developmental-arrestive protein. See Taylor et al., (1994), who described enzymatic inactivation in transgenic tobacco via production of single-chain antibody fragments.

F. Modified Fatty Acid, Phytate and Carbohydrate Metabolism

Genes may be used conferring modified fatty acid metabolism. For example, stearyl-ACP desaturase genes may be used. See Knutzon et al., (1992). Various fatty acid desaturases have also been described, such as a *Saccharomyces cerevisiae* OLE1 gene encoding Δ9 fatty acid desaturase, an enzyme which forms the monounsaturated palmitoleic (16:1) and oleic (18:1) fatty acids from palmitoyl (16:0) or stearoyl (18:0) CoA (McDonough et al., 1992); a gene encoding a stearoyl-acyl carrier protein delta-9 desaturase from castor (Fox et al. 1993); Δ6- and Δ12-desaturases from the cyanobacteria *Synechocystis* responsible for the conversion of linoleic acid (18:2) to gamma-linolenic acid (18:3 gamma) (Reddy et al. 1993); a gene from *Arabidopsis thaliana* that encodes an omega-3 desaturase (Arondel et al. 1992)); plant Δ9-desaturases (PCT Application Publ. No. WO 91/13972) and soybean and *Brassica* Δ15 desaturases (European Patent Application Publ. No. EP 0616644).

Phytate metabolism may also be modified by introduction of a phytase-encoding gene to enhance breakdown of phytate, adding more free phosphate to the transformed plant. For example, see Van Hartingsveldt et al., (1993), for a disclosure of the nucleotide sequence of an *Aspergillus niger* phytase gene. In corn, this, for example, could be accomplished by cloning and then reintroducing DNA associated with the single allele which is responsible for corn mutants characterized by low levels of phytic acid. See Raboy et al., (1990).

A number of genes are known that may be used to alter carbohydrate metabolism. For example, plants may be transformed with a gene coding for an enzyme that alters the branching pattern of starch. See Shiroza et al., (1988) (nucleotide sequence of *Streptococcus mutans* fructosyltransferase gene), Steinmetz et al., (1985) (nucleotide sequence of *Bacillus subtilis* levansucrase gene), Pen et al., (1992) (production of transgenic plants that express *Bacillus licheniformis* α-amylase), Elliot et al., (1993) (nucleotide sequences of tomato invertase genes), Sergaard et al., (1993) (site-directed mutagenesis of barley α-amylase gene), and Fisher et al., (1993) (maize endosperm starch branching enzyme II). The Z10 gene encoding a 10 kD zein storage protein from maize may also be used to alter the quantities of 10 kD Zein in the cells relative to other components (Kirihara et al., 1988).

III. Plants and Use Thereof

The present invention provides a transgenic plant comprising a plant minichromosome of the invention including, without limitation, alfalfa, corn, canola, rice, soybean, tobacco, turfgrass, oat, rye, and wheat, among others. Also included is a seed from a plant, the seed comprising a minichromosome of the invention.

For example, in certain embodiments, a seed comprising a minichromosome of the invention may express a gene that provides for herbicide tolerance. One beneficial example of a herbicide tolerance gene provides resistance to glyphosate, N-(phosphonomethyl)glycine, including the isopropylamine salt form of such herbicide.

The present invention can be, in practice, combined with other disease control traits in a plant to achieve desired traits for enhanced control of plant disease. Combining disease control traits that employ distinct modes-of-action can provide protected transgenic plants with superior consistency and durability over plants harboring a single control trait because of the reduced probability that resistance will develop in the field.

The invention also relates to commodity products containing one or more of the minichromosomes of the present invention, and produced from a recombinant plant or seed containing one or more minichromosome. A commodity product containing one or more of the sequences of the present invention is intended to include, but not be limited to, meals, oils, crushed or whole grains or seeds of a plant, or any food product comprising any meal, oil, or crushed or whole grain of a recombinant plant or seed containing one or more of the sequences of the present invention. The detection of one or more of the sequences of the present invention in one or more commodity or commodity products contemplated herein is de facto evidence that the commodity or commodity product comprises a minichromosome of the invention.

A further aspect of the invention relates to tissue cultures of plants comprising mini-chromosomes. As used herein, the term "tissue culture" indicates a composition comprising isolated cells of the same or a different type or a collection of such cells organized into parts of a plant. Exemplary types of tissue cultures are protoplasts, calli and plant cells that are intact in plants or parts of plants, such as embryos, pollen, flowers, kernels, ears, cobs, leaves, husks, stalks, roots, root tips, anthers, silk, and the like. In a preferred embodiment, the tissue culture comprises embryos, protoplasts, meristematic cells, pollen, leaves or anthers derived from immature tissues of these plant parts. Means for preparing and maintaining plant tissue cultures are well known in the art (U.S. Pat. Nos. 5,538,880; and 5,550,318, each incorporated herein by reference in their entirety). By way of example, a tissue culture comprising organs such as tassels or anthers has been used to produce regenerated plants (U.S. Pat. Nos. 5,445,961 and 5,322,789; the disclosures of which are incorporated herein by reference).

One type of tissue culture in maize is tassel/anther culture. Tassels contain anthers which in turn enclose microspores. Microspores develop into pollen. For anther/microspore culture, if tassels are the plant composition, they are preferably selected at a stage when the microspores are uninucleate, that is, include only one, rather than 2 or 3 nuclei. Methods to determine the correct stage are well known to those skilled in the art and include mitramycin fluorescent staining, trypan blue (preferred) and acetocarmine squashing. The mid-uninucleate microspore stage has been found to be the developmental stage most responsive to the subsequent methods disclosed to ultimately produce plants.

Although microspore-containing plant organs such as tassels can generally be pretreated at any cold temperature below about 25° C., a range of 4 to 25° C. is preferred, and a range of 8 to 14° C. is particularly preferred. Although other temperatures yield embryoids and regenerated plants, cold temperatures produce optimum response rates compared to pretreatment at temperatures outside the preferred range. Response rate is measured as either the number of embryoids or the number of regenerated plants per number of microspores initiated in culture. Exemplary methods of microspore culture are disclosed in, for example, U.S. Pat. Nos. 5,322,789 and 5,445,961, the disclosures of which are specifically incorporated herein by reference.

Furthermore, in certain embodiments of the invention, a starting plant or plant cell is transformed with a nucleic acid such as a telomere truncation vector. Methods for transforming plant cells with nucleic acids are well known to those of skill in the art. For example, methods may employ *Agrobacterium* mediated transformation or DNA particle bombardment as exemplified herein. Certain specialized methods for transforming high molecular weight nucleic acids have also been developed. For instance, the BIBAC system designed by Hamilton and colleagues (Hamilton, 1997; Hamilton et al., 1996; U.S. Pat. No. 5,733,744) for the transformation of large T-DNA inserts to plant genomes. The BIBAC is a combination of the T-DNA transfer function of the Ti plasmid and the capacity of maintaining large DNA fragments of the bacterial artificial chromosome (BAC). As with a BAC, it has a single copy origin of replication from the *E. coli* F-plasmid for stable maintenance of the plasmid in *E. coli*. It also has a single copy origin of replication from the *Agrobacterium* Ri plasmid, and the T-DNA borders for T-DNA transformation. A similar system, transformation competent artificial chromosomes (TAC), with an *E. coli* bacteriophage P1 origin, has also been used in the transformation of large DNAs (Liu et al., 1999).

IV. Breeding of Plants Comprising a Minichromosome

As discussed above a starting, native plant chromosome may be used in accordance with the invention to generate a plant minichromosome. In some embodiments, native chromosomes for use in the current invention will be maize chromosomes such as maize B chromosomes or a maize A chromosome. For example, any of the *Z. mays* chromosomes listed in Table 1 may be used as a starting chromosome for making a minichromosome of the invention.

Table 1 illustrates the sizes for *Zea mays* A chromosomes in Megabase pairs (Mb) or in centimorgans (cM). The size in cM has determined via two different strategies as described in Sharopova et al., 2002.

TABLE 1

*Zea mays* A chromosome sizes.

| Chromosome | Size | | |
|---|---|---|---|
| | Mega base pairs (Mb) | IBM v2 (cM) | UMC98 (cM) |
| 1 | 337 | 975 | 248 |
| 2 | 278 | 612 | 207 |
| 3 | 259 | 685 | 166 |
| 4 | 271 | 684 | 175 |
| 5 | 250 | 607 | 174 |
| 6 | 208 | 492 | 168 |
| 7 | 199 | 566 | 147 |
| 8 | 202 | 567 | 183 |
| 9 | 191 | 581 | 150 |
| 10 | 170 | 472 | 134 |

It will also be understood that in some cases the minichromosome comprises a site specific recombination site. Thus, any plant variety comprising the minichromosome may be transformed with a vector that enables the introduction of transgene into the minichromosome by site specific recombination. Once a plant minichromosome is generated it may be easily introgressed into a desired genetic background by plant breeding techniques that are well know in the art.

Thus, the present invention provides processes for breeding of plants that comprise a minichromosome. In accordance with such a process, a first parent plant may be crossed with a second parent plant wherein the first and second plants comprise a minichromosome, or wherein at least one of the plants comprises a minichromosome. For example, corn plants (*Zea mays* L.) comprising a minichromosome can be crossed by either natural or mechanical techniques.

Natural pollination occurs in flowering plants when wind or insects spread pollen from a plant. However, mechanical pollination can be effected by controlling the types of pollen that are introduced or by pollinating by hand. In one embodiment, crossing comprises the steps of:

(a) planting in pollinating proximity seeds of a first and a second parent plant, and preferably, seeds of a first inbred plant and a second, distinct inbred plant;

(b) cultivating or growing the seeds of the first and second parent plants into plants that bear flowers;

(c) emasculating flowers of either the first or second parent plant, i.e., treating the flowers so as to prevent pollen production, or alternatively, using as the female parent a male sterile plant, thereby providing an emasculated parent plant;

(d) allowing natural cross-pollination to occur between the first and second parent plants;

(e) harvesting seeds produced on the emasculated parent plant; and, where desired, (f) growing the harvested seed into a plant, preferably, a hybrid plant.

Parental plants are typically planted in pollinating proximity to each other by planting the parental plants in alternating rows, in blocks or in any other convenient planting pattern. Where the parental plants differ in timing of sexual maturity, it may be desired to plant the slower maturing plant first, thereby ensuring the availability of pollen from the male parent during the time at which the female parent is receptive to pollen. Plants of both parental parents are cultivated and allowed to grow until the time of flowering. Advantageously, during this growth stage, plants are in general treated with fertilizer and/or other agricultural chemicals as considered appropriate by the grower.

At the time of flowering, in the event a plant comprising a minichromosome is the male parent, the pollen producing organs of the other parental plant are removed from all plants employed as the female parental plant to avoid self-pollination. This can be achieved manually but also can be done by machine, if desired. Alternatively, when the female parent plant comprises a cytoplasmic or nuclear gene conferring male sterility, removal of the pollen producing organs may not be required. Additionally, a chemical gametocide may be used to sterilize the male flowers of the female plant. In this case, the parent plants used as the male may either not be treated with the chemical agent or may comprise a genetic factor which causes resistance to the emasculating effects of the chemical agent. Gametocides affect processes or cells involved in the development, maturation or release of pollen. Plants treated with such gametocides are rendered male sterile, but typically remain female fertile. The use of chemical gametocides is described, for example, in U.S. Pat. No. 4,936,904, the disclosure of which is specifically incorporated herein by reference in its entirety. Furthermore, the use of ROUNDUP herbicide (Monsanto, St. Louis, Mo.) in combination with glyphosate tolerant corn plants to produce male sterile corn plants is disclosed in PCT Publication WO 98/44140.

Following emasculation, the plants are then typically allowed to continue to grow and natural cross-pollination occurs as a result of the action of wind, which is normal in the pollination of grasses, such as corn. As a result of the emasculation of the female parent plant, all the pollen from the male parent plant is available for pollination because pollen bearing flowering parts, have been previously removed from all plants of the plant being used as the female in the hybridization. Of course, during this hybridization procedure, the parental varieties are grown such that they are isolated from other plant fields to minimize or prevent any accidental contamination of pollen from foreign sources. These isolation techniques are well within the skill of those skilled in this art.

Both parental plants of a cross may be allowed to continue to grow until maturity or the male rows may be destroyed after flowering is complete. Only the seeds from the female parental plants are harvested to obtain the seeds of a novel $F_1$ hybrid. The novel $F_1$ hybrid seed produced can then be planted in a subsequent growing season in commercial fields or, alternatively, advanced in breeding protocols for purposes of developing novel inbred lines.

Alternatively, in another embodiment of the invention, one or both first and second parent plants can comprise a plant minichromosome. Thus, any plant comprising a minichromosome of the invention forms a part of the invention. As used herein, crossing can mean selfing, backcrossing, crossing to another or the same variety, crossing to populations, and the like. All corn plants produced using plant comprising a minichromosome as a parent are, therefore, within the scope of this invention.

EXAMPLES

The following examples are included to further illustrate various aspects of the invention. It should be appreciated by those of skill in the art that the techniques disclosed in the examples that follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

General Telomere Truncation Methods

Telomere-mediated chromosomal truncation is accomplished by the introduction of six copies of telomere repeats into an endogenous plant chromosome via a transformation plasmid. In this particular case the telomere repeats were made from *Arabidopsis* telomeres previously cloned by Richards and Ausubel (1988). Maize HiII (Armstrong and Green, 1985) immature embryos were transformed following the protocols for *Agrobacterium*-mediated transformation with a standard binary vector (Frame et al., 2002). During the *Agrobacterium*-mediated transformation, the T-DNA is protected by *Agrobacterium* VirD2 and VirE proteins, and integrated into the plant genome by an illegitimate recombination mechanism. Small deletions may occur mostly in the left border region, and sometimes in the right border region. However, these deletions will not destroy the telomere sequence. The presence of the telomere repeats truncates the chromosome upon integration. The telomere-associated chromosome truncation has been demonstrated to occur, and has been used to produce minichromosomes in mammalian cells (Farr et al., 1991, 1992, 1995; Barnett et al., 1993; Itzhaki et al., 1992; Heller et al., 1996; Mills et al., 1999; Saffery et al., 2001). Using two telomere-mediated chromosomal truncation constructs, it was demonstrated that six copies of direct *Arabidopsis* telomere units could render chromosomal truncation in maize.

Figure 1:
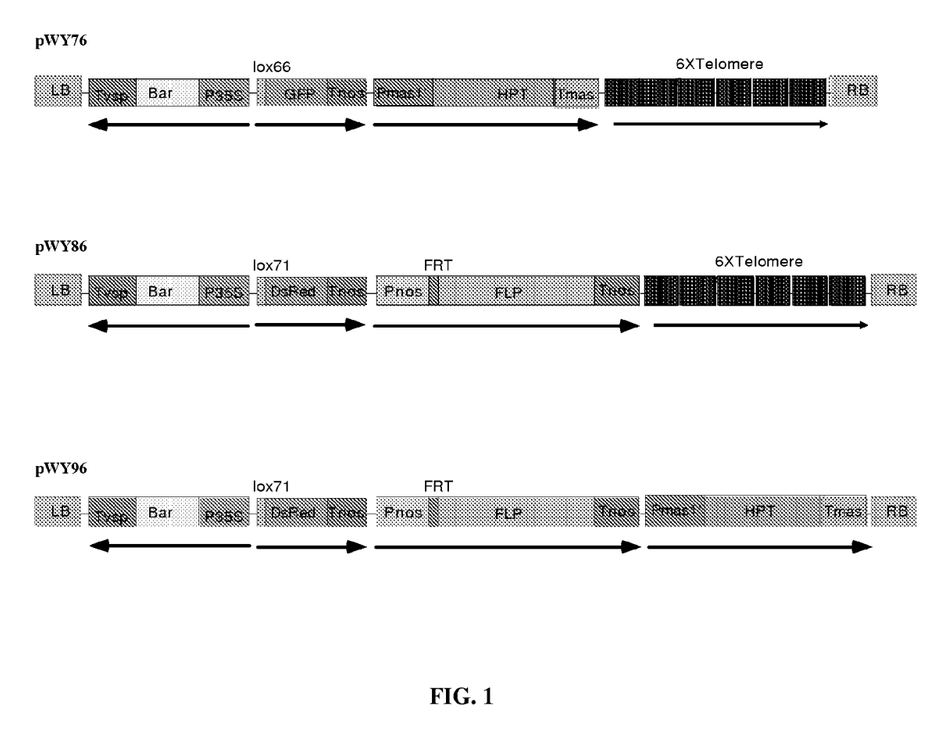

Two binary constructs for chromosomal truncation were constructed for *Agrobacterium*-mediated gene transformation of maize HiII immature embryos (pWY76 and pWY86; see FIG. 1). Ninety three and eighty three transgenic lines were recovered for pWY76 and pWY86, respectively. A fluorescence in situ hybridization (FISH) method (Kato et al., 2004) was used to detect transgenes on metaphase chromosomes of T0 transgenic plants. A total of 123 transgene integration sites for pWY76 and 107 sites for pWY86 were visualized, with 54 and 55 integration sites localized at the ends of chromosomes. Pollen abortion was also observed in transgenic lines in which chromosomal truncation occurred. Furthermore, deletions of distal FISH markers in several transgenic lines were detected by a karyotyping probe cocktail. For example, in one pWY76 transgenic line, the chromosome 3 short arm was truncated. Southern blot analysis demonstrated smear patterns of hybridization, which is a typical feature of heterogeneous newly seeded telomeres (Farr et al., 1991). These studies indicated that chromosome truncations occurred in these transgenic lines. In contrast to the pWY76 and pWY86 transgenes, two other constructs without the telomere repeats were also transformed simultaneously; however, no chromosomal truncations observed. These results indicated that the telomere repeats were the cause of chromosome truncation.

An A chromosome derived mini-chromosome was found in one pWY86 line by FISH screening. This mini-chromosome was found to originate from chromosome 7 with most of the long arm deleted. This mini-chromosome was originally found in a tetraploid line without B chromosomes. Because it occurred in a polyploid, the deficiency caused by the truncation of the chromosome was compensated by its homologues in diploid gametophytes. In fact, the typical 50% pollen abortion observed in diploid lines with one chromosome deficiency was not observed, and progenies containing this minichromosome were recovered after crossing the recovered transformant by a diploid plant, which reduced the ploidy level to triploid. The ploidy level was further reduced to diploid plus the minichromosome in both HiII and Mo17 backgrounds. Further studies showed that this minichromosome did not cause any abnormal phenotypes. The minichromosome transmitted at 38.5% (10/26) rate as male when crossed to a diploid plant.

Nucleic Acid Constructs for Telomere Truncation in Plants

Two truncating constructs and a telomere-minus control were constructed by using the binary vector pTF101.1 (Paz et al., 2004) and used for the minichromosome production (see FIG. 1 for maps of constructs). Components on these constructs are listed in order as below: pWY76: LB-Tvsp-Bar-2XP35S-lox66-GFP-Tnos-Pmas-HPT-Tmas-6x telomeres-RB, pWY86: LB-Tvsp-Bar-2XP35S-lox 71-DsRed-Tnos-Pnos-FRT-FLP-Tnos-6x telomeres-RB and pWY96: LB-Tvsp-Bar-2XP35S-lox 71-DsRed-Tnos-Pnos-FRT-FLP-Tnos-Pmas-HPT-Tmas-RB Promoterless lox66-GFP, or lox71-DsRed fusion genes were included in pWY76 and pWY86, respectively, to allow further gene specific integration at the lox site. In addition, a Pnos-FRT-FLP-Tnos cassette was included in pWY86 to allow site-specific recombination at the FRT site for further gene integration.

Example 2

Telomere Truncation in B-Chromosomes

To produce mini-B chromosomes by telomere-mediated chromosomal truncation, B chromosomes from Black Mexican Sweet (BMS) corn cells were introduced into a maize HiII parent A line and allowed to accumulate to multi-copies. The two telomere-associated chromosomal truncation constructs were mixed with a pACH25 construct (Christensen and Quail, 1996) for targeting HiII hybrid or HiII parent A immature embryos with multiple B chromosomes by biolistic transformation (Frame et al., 2000). The bar gene driven by a maize ubiquitin promoter in the pACH25 construct enables efficient selection of transgenic events on media supplemented with bialaphos. Telomere sequences on the constructs truncate B chromosomes as well as A chromosomes once integrated into the chromosomes, thus both minichromosomes from truncated B and A chromosomes can be produced. Root tip metaphase chromosomes obtained from regenerated herbicide resistant plants (T0) were screened by FISH for minichromosomes. The pACH25 plasmid and a pWY96 construct (see Example 1), which has almost all other sequences of both pWY76 and pWY86 (see below) except the telomere sequence, are used as probes for FISH screening. The pWY96 probe can efficiently hybridize with both the pWY76 and pWY86 transgenes. A B-repeat probe was used to identify truncations of the B chromosomes (Alfenito and Birchler, 1993). Forty eight minichromosomes were identified; 41 of which were from the B chromosome while 7 were from an A chromosome. All minichromosomes from B chromosomes were transmissible and most of them were recovered in the T1 generation. A chromosome doubling treatment (Kato and Birchler, 2006) was conducted on three truncated A minichromosomes to preserve the minichromosomes as they would otherwise be lost in meiosis if maintained in a diploid.

Example 3

Figure 2:
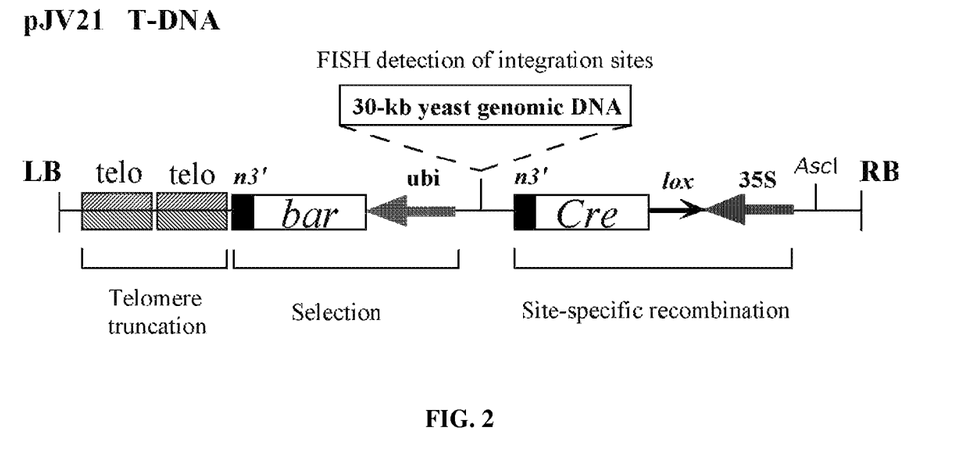

Expression of Cre Gene by *Agrobacterium*-Mediated Gene Transformation with a BIBAC Vector System A BIBAC™ system was adopted for maize transformation with a large piece of genetic material including a herbicide resistance marker gene, a 30 kb yeast genomic DNA as a marker for fluorescence in situ hybridization (FISH), and a 35S-lox-Cre recombination cassette. Briefly, the BIBAC gene transformation plasmid pJV21 was constructed as follows. The pCH20 vector (Hamilton, 1997) was modified to deleted the BamHI to SwaI fragment. The BamHI site was reconstituted by adding a BamHI linker at the SwaI site followed with BamHI digestion and re-ligation. The resulting plasmid is named pJV06. A 3.4 kb HindIII/SalI fragment containing the 35S-loxP-Cre gene expression cassette from pED97 was cloned into the BamHI site by blunt end ligation to make pJV08. Next, a 400 bp telomere sequence and a ubi-bar gene expression cassette from pAHC25 (Christensen et al., 1992) were assembled in pBLUESCRIPT™ (Strategene, La Jolla, Calif.) and then cloned into the SrfI site of pJV08 by blunt end ligation to make pJV15 in which the telomere sequence was placed at the left border of the binary vector. The ubi-bar gene was used as a selection marker for these studies. The telomere sequence TTTAGGG (SEQ ID NO:1) was orientated towards the left border. Another 400 bp telomere sequence was cloned into the PacI site by blunt end ligation to make a direct repeat of the 800 bp of telomere sequence at the LB. The clone was sequenced to confirm the orientation of the telomere repeat. A 30 kb yeast DNA from BIBAC1 (Hamilton, 1997; Hamilton et al., 1996) was then cloned into the NotI site to make pJV21 (FIG. 2). Constructs were transferred to *Agrobacterium* strain LBA4404 by electroporation of competent cells following the manufacturer's instructions (Gibco, Invitrogen Co., Carlsbad, Calif.). In this construct, a 35S-lox66-Cre cassette was cloned adjacent to the right border in order to place the Cre/lox site-specific recombination system into the genome by gene transformation.

Genetic Transformation

An *Agrobacterium*-mediated gene transformation was performed with the pJV21 construct to transform immature embryos of HiII plants with 0 to 12 B chromosomes. Seventy-five transformed lines were recovered. The transgenes were confirmed by Southern hybridization and FISH (Kato et al., 2004). In 60 lines characterized by Southern hybridization, 45 lines had a single copy transgene. Sixty-three of the 75 transgenic lines had a single transgene as determined by FISH. The transgene integrity was analyzed by Southern blot hybridizations at both the left and the right ends of the T-DNA region using probes of the bar gene and the Cre gene, respectively. In the 75 lines that were analyzed, 52 transgenic lines were found to have the same copy number at both the left and the right border, indicating that the transgenes in these cases are intact.

Integration of a Transgene into the Telomere Region

One transgenic event J11-9 showed a smear pattern of Southern hybridization as compared to the others that have discrete bands. The smear pattern of hybridization is a hallmark of telomeres that result from natural telomere activity or neo-telomeres seeded during a telomere-mediated chromosomal truncation, because the telomerase adds different numbers of the telomeric motif TTTAGGG; (SEQ ID NO:1) in different cells (Farr et al., 1991; Richards and Ausubel, 1988). To demonstrate the terminal nature of this transgene, multiple restriction enzymes that cut the distal region of the transgene just preceding the 800 bp telomere repeat were used to digest the J11-9 genomic DNA, and a Southern hybridization was performed with a $^{32}$P-labeled bar gene probe as described (Yu et al., 2006b). The smear patterns of hybridization shifted according to the distances between the three restriction enzyme cutting sites (XbaI, XhoI and DraI) and the telomeric ends of the chromosome. For example, the most proximal enzyme DraI generated the largest sized smear pattern in the range of more than 6 kb, while the most distal one XbaI generated a smear patterns in the range of 3.2 to 4.6 kb and the XhoI produced smears between 5 to 6 kb. In contrast, the cleavage at a more proximal HindIII site produced a discrete band. A discrete band would be generated if there is a HindIII site distal to the bar gene probe. This HindIII site was likely present at the natural telomere because this site was not found in our sequence data of the pJV21 construct. Thus, the end position of the transgene in J11-9 was potentially the result of an integration event within the telomeres rather than a de novo telomere formation. In addition, no abnormal growth, gametophyte sterility, or reduced transmission has been observed in the J11-9 plants, indicating that there is no functional genetic material loss caused by this transgene, a phenomenon frequently observed in transgenic plants with chromosomal truncations (Yu et al., 2006b).

The end location of this transgene was also revealed by a cytological analysis. Chromosomes from J11-9 root tips were hybridized with a Fluorescein-dUTP labeled 30 kb DNA probe mixed with a karyotyping cocktail (Kato et al., 2004). The karyotypes of HiII transformation recipients were produced with this cocktail (Yu et al., 2006a). The transgene was identified at the end of chromosome arm 3L.

Position and the Distribution of Transgenes

The FISH analysis was extended to all the transgenic lines in order to profile the transgene positions and distributions. Transgenes were found in every chromosome of the karyotype (Table 2) and integration sites were found in or near telomeres, centromeres, euchromatic regions, heterochromatic knobs and NOR regions by FISH. All chromosome arms were included except 8S and 10S. The transgenes were distributed randomly among the 10 A chromosomes with greater numbers on large chromosomes, and less numbers on small chromosomes as expected. However, no transgene was observed on any B chromosome although there were up to 12 B chromosomes ("Bs") present (average 3.9) in the transformed plants.

TABLE 2

Transgenic events with the pJV21 construct of maize by *Agrobacterium*-mediated transformation.

| Trans. Line | Bs | Southern bar | Cre | FISH Y30 | Cre Activity | Chromosome location |
|---|---|---|---|---|---|---|
| 10-1 | 4 | 1 | 1 | 1 | + | 1L, Satellite |
| 10-2 | 5 | 1 | 1 | 1 | + | 1S |
| 10-3 | 1 | 1 | 1 | 1 | + | 1S, Distal |
| 10-4 | 3 | 1 | 1 | 1 | + | 1S |
| 10-5 | 3 | 1 | 2 | 1 | + | 5S, Distal |
| 10-6 | 4 | 1 | 0 | 1 | + | 6L |
| 10-7 | 2 | 1 | 0 | 1 | − | 10L, Very Distal |
| 11-1 | 4 | 1 | 1 | 1 | + | 7L, Cent.-Knob-Y30 |
| 11-2 | 0 | 1 | 1 | 2 | + | 2L + 7L, 2L = Sat.-Y30-5SRNA, 7L = Distal |
| 11-3 | 6 | 3 | 3 | 3 | + | 2C + 4S + 5L, 2C = Centromeric, 4S = Satellite, 5L = Middle |
| 11-5 | 3 | 1 | 1 | 1 | + | 5L, Sat.-Y30-Knob |
| 11-6 | 4 | 1 | 2 | 1 | + | 2S, Cent.-Y30-Sat. |
| 11-7 | 6 | 1 | 1 | 1 | + | 1L |
| 11-8 | 3 | 2 | 3 | 1 | + | 1S, Cent.-Y30-Knob |
| 11-9 | 5 | 1 | 1 | 2 | + | 3L + 5L, 3L = Very Distal, 5L = Distal |
| 11-10 | 8 | 1 | 0 | 1 | − | 10L, Distal |
| 11-11 | 3 | 2 | 1 | 1 | + | 7L, Knob |
| 11-12 | 1 | 1 | 1 | 1 | + | 1L, Distal |
| 11-13 | 2 | 1 | 1 | 1 | + | 7L, Distal |
| 11-14 | 4 | 1 | 1 | 1 | + | 1L |

TABLE 2-continued

Transgenic events with the pJV21 construct of maize by *Agrobacterium*-mediated transformation.

| Trans. Line | Bs | Southern bar | Cre | FISH Y30 | Cre Activity | Chromosome location |
|---|---|---|---|---|---|---|
| 11-15 | 3 | 3 | 1 | 1 | + | 1S, Middle |
| 11-16 | 4 | 3 | 1 | 1 | + | 6L, Middle |
| 11-17 | 6 | 2 | 2 | 2 | + | 7L + 7S, 7L = Cent.-Y30-Knob |
| 11-18 | 6 | 1 | 2 | 1 | + | 3S, Distal |
| 11-19 | 2 | 1 | 1 | 1 | + | 7L |
| 11-20 | 5 | 1 | 1 | 1 | + | 9S, Cent.-Y30-Knob |
| 11-21 | 5 | 3 | 0 | 1 | − | 2C, Centromeric |
| 11-22 | 3 | 2 | 0 | 1 | − | |
| 11-23 | 8 | 1 | 2 | 1 | + | 1L, Satellite |
| 11-24 | 7 | 1 | 1 | 1 | + | 7L |
| 11-25 | 7 | 1 | 1 | 1 | + | 3L, Distal |
| 11-26 | 2 | 2 | 2 | 2 | + | 2L + 9L, 2L = Middle, 9L = Distal |
| 11-27 | 6 | 1 | 1 | 1 | + | 10L, Distal |
| 11-28 | 4 | 1 | 1 | 1 | + | 5L, Distal |
| 11-29 | 9 | 1 | 2 | 1 | + | 3S, Distal |
| 11-30 | 1 | 1 | 1 | 1 | + | 5L, Knob |
| 11-31 | 4 | 1 | 1 | 2 | + | 7L + 10L, 7L = Knob, 10L = Very Distal |
| 11-32 | 2 | 1 | 1 | 1 | + | 4L, Distal |
| 12-1 | 6 | 1 | 1 | 2 | + | 2L + 7S |
| 12-2 | 3 | 3 | 3 | 1 | − | 3S |
| 12-3 | 11 | 2 | 2 | 2 | + | 4L, Middle |
| 12-4 | 6 | 1 | 1 | 1 | + | 9L, Distal |
| 12-5 | 5 | 1 | 2 | 1 | + | 7L, Distal |
| 12-6 | 0 | 1 | 1 | 1 | + | 8L, Very Distal |
| 12-7 | 2 | 1 | 1 | 1 | + | 5L |
| 12-8 | 0 | 1 | 2 | 1 | + | 1L + 3L + 6S, 1L = Distal to Sat. |
| 12-9 | 2 | 1 | 1 | 1 | + | 4S, Proximal to Sat. |
| 12-10 | 1 | 1 | 1 | 1 | + | 2S, Distal |
| 12-11 | 5 | 1 | 1 | 1 | + | 9L, Middle |
| 12-12 | 0 | 1 | 1 | 1 | + | 5L, Distal |
| 12-13 | 2 | 1 | 1 | 1 | + | 4S, Cent.-Y30-Sat. |
| 12-14 | 2 | 1 | 1 | 1 | + | 8L, Knob |
| 12-15 | 2 | 1 | 0 | 1 | + | 4L, Middle |
| 12-16 | 11 | 1 | 1 | 1 | + | 3L, Middle |
| 12-17 | 6 | 1 | 1 | 1 | + | 4L, Middle |
| 12-18 | 6 | 1 | 1 | 1 | + | 5L, Middle |
| 12-19 | 4 | 3 | 3 | 1 | + | 6L, Distal |
| 12-20 | 6 | 4 | 2 | 2 | + | 1L + 10L, 1L = In the Sat., 10L = Distal |
| 12-21 | 0 | 2 | 1 | 1 | + | 2L, Middle |
| 12-22 | 3 | 2 | 1 | 1 | + | 3L, Middle |
| 12-23 | 1 | 1 | 0 | 0 | − | |
| 12-24 | 7 | 1 | 1 | 1 | + | 8L, Knob |
| 12-25 | 4 | 1 | 2 | 1 | + | 2L, Cent.-Sat.-Y30 |
| 12-26 | 5 | 1 | 1 | 1 | + | 10L, Distal |
| 12-27 | 9 | 1 | 1 | 1 | + | 1S, Middle |
| 12-28 | 3 | 1 | 1 | 1 | + | |
| 12-29 | 2 | 1 | 1 | 1 | + | 3L, Middle |
| 12-30 | 5 | 1 | 0 | 1 | + | 1L |
| 12-31 | 4 | 1 | 1 | 1 | + | 6S, NOR |
| 12-32 | 4 | 1 | 1 | 1 | + | 3S, Distal |
| 12-33 | 2 | 1 | 1 | 1 | + | 3L, Middle |
| 12-34 | 3 | 1 | 1 | 1 | + | 2S, Distal |
| 12-35 | 4 | 1 | 1 | 1 | − | 8L, Cent.-Y30-Knob |
| 12-36 | 0 | 1 | 1 | 1 | + | 8L |
| 12-37 | 2 | 1 | 1 | 2 | + | 1S + 6L, 1S = Knob, 6L = Distal |

Cre/Lox Site-Specific Recombination System

The transformation with the BIBAC construct placed 84 transgenes randomly into the maize genome. These transgenes are mostly intact as indicated by Southern hybridizations. Ninety-one transgenic sites were detected in 75 transgenic lines by Southern hybridizations with a Cre gene probe (Table 2). To demonstrate that these Cre transgenes were expressed and functional, a reporter construct pHK52 (Srivastava et al., 1999) was biolistically delivered into the immature embryos of the progeny of the transgenic plants.

The pHK52 construct contains an antisense orientated beta-glucuronidase (GUS) gene under the maize ubiquitin promoter. The antisense GUS gene is flanked by inverted repeats of the loxP site. The antisense GUS gene can be reverted to the sense orientation and expressed at the presence of a Cre recombinase which catalyzes the inversion of genetic elements flanked by inverted repeats of lox sites. A transient GUS assay was performed on bombarded embryos from all transgenic lines. This study demonstrated the Cre gene was functional in 68 lines (Table 2). An embryo population was segregating for the transgene in an outcross of J11-9 to the Hill line. GUS expression was activated in 30 out of a total of 50 embryos, a ~1:1 ratio.

Example 4

Telomere Truncation of B Chromosomes by Particle Bombardment Transformation

Since the B-chromosome has many properties that make it preferable for as a minichromosome, further studies were performed to determine whether plant minichromosomes derived from B chromosomes may be efficiently generated. Telomere truncation constructs, pWY76 and pWY86 (FIG. 1) were used in these studies. Additionally, plasmid pWY86-bar was made by digesting pWY86 with PmlI/AvrII and self-ligation to delete the 35S-bar gene expression cassette. Plasmid pAHC25 used in the studies has been previously described by Christensen and Quail (1996).

Briefly, immature embryos between 1.2 to 2.0 mm were dissected aseptically in a flow hood. Biolistic-mediated gene transformation of maize immature embryos was conducted as described by Songstad et al. (1996) and Frame et al. (2000). Immature embryos were placed face down on callus initiation media with N6 salts and vitamins (Chu et al., 1975) supplemented with 2.0 mg/l 2, 4-D, 100.0 mg/l myo-inositol, 2.8 g/l proline, 30.0 g/l sucrose, 100.0 mg/l casein hydrolysate, 3.0 g/l GELRITE, 25 µM silver nitrate, PH 5.8. Embryos were induced at 28° C. for 2-4 days, then transferred to osmotic media with N6 salts and vitamins supplemented with 2.0 mg/l 2, 4-D, 100.0 mg/l myo-inositol, 0.7 g/l proline, 30.0 g/l sucrose, 100.0 mg/l casein hydrolysate, 36.4 g/l sorbitol, 36.4 g/l mannitol, 3.0 g/l GELRITE, 25 µM silver nitrate, pH 5.8 for 4 hours osmotic treatment prior to bombardment.

Plasmids were prepared with a Qiagen miniprep kit (Qiagen, Valencia, Calif.). Three milligrams of 0.6µ gold particles (BIO-RAD, Hercules, Calif.) were coated with the mixture of 1 µg telomere truncation plasmid (pWY76, pWY86, or pWY86-bar) and 0.25 µg pAHC25. The bombardment was carried out with the PDS 1000/He biolistic gun (BIO-RAD) using the following parameters: 650 psi rupture disk pressure, 6 cm target distance, 6 mm gap, 1.2 cm from macro-carrier to stopping plate, and 28 Ton vacuum at rupture.

Bombarded embryos on the osmotic media were wrapped with PARAFILM and incubated at 28° C. overnight and then transferred to callus initiation media the next morning.

FISH Analysis of Mini-Chromosomes in Transgenic Plants

T0 transgenic plants were screened for mini-chromosomes by FISH as described above. Probes of pWY96 and pAHC25 were labeled with Texas red dCTP by nick translation (Kato et al., 2004) and hybridized to transgenes. B repeat sequence (Alfenito and Birchler 1993) was labeled with Alexa Fluor-488 dCTP, and mixed with either pWY96 or pAHC25 transgene probes to screen transformed B chromosomes by biolistic-mediated transformation. CentC (Ananiev et al., 1998) and NOR (Stein et al., 1998) probes were labeled with Alexa Fluor-488 dCTP (Invitrogen); CRM (Zhong et al., 2000) was labeled with Cy5-dCTP. Minichromosomes were identified by their size as compared to normal A or B type chromosomes. FISH of meiotic cells was performed as described by Gao et al. (1999) and Yu et al. (2006). B repeat was labeled with Texas red dCTP and the knob sequence (14) was labeled green with Alexa Fluor-488 dCTP.

Two hundred eighty one transgenic events were regenerated from bialaphos resistance calli (67 with pWY76, 87 with pWY86, and 127 with pWY86-bar). FISH revealed that forty one events had transgenes on B chromosomes, which included 24 mini-chromosomes with distal transgenes and 20 intact B chromosomes with internal transgenes. Additionally, 5 A-B and 1 B-A translocations, and 7 fragments from A chromosomes were identified. Finally, 10 truncated B chromosome derivatives without transgene signals were also identified. These events were likely produced when telomere-mediated chromosomal truncation occurred in such an orientation that the transgenes are retained on acentric fragments and are lost during mitosis. These mini-chromosomes would be lost during selection in the transformation process if they had not been supported by additional transgenes in the same event. Thus, these minichromosomes were fewer in number than those with transgenes.

Minichromosome Size Measurement

To measure the size of the B centromere repeat of 86B23, the green channels of 10 metaphase chromosome images that has B repeat labeled green were imported to the Fujifilm Image Gauge V3.3 program (Fuji, Tokyo, Japan). The quantity of the minichromosome centromere and that of a normal B chromosome centromere were measured and the ratio of the mini-chromosome centromere to that from a normal B was calculated from each individual cell. The average ratio and standard deviation were calculated. To measure the chromosome size of 86B23, the pachytene chromosomes were stained with 4'-6-Diamidino-2-phenylindole (DAPI), images were captured via a Zeiss fluorescence microscope (Carl Zeiss, Inc., Oberkochen, Germany) and imported to Fujifilm Image Gauge program (Fuji). The lengths of the mini-chromosome and the normal B chromosome were measured, and their ratio was calculated. The sizes of other mini-chromosomes were estimated visually based on their appearance as compared with those of normal B chromosomes in the same cell. Size comparisons of several truncated B chromosomes are shown in Table 3.

Transmission Test of Mini-Chromosomes

Results from these studies showed that transmission of mini-chromosomes during meiosis varies (Table 3). The transmission of a univalent R2 (34.8% from a self-pollination) was comparable with a previously reported isochromosome 8S•8S (37.5%) (Yu et al., 2006). The transmission of B type mini-chromosomes varies from 12% (86-74) to 39% (76-15a) via the male parent (Table 3). Transmission of mini-chromosomes was affected by many factors, such as a chromosome size limit (Schubert, 2001; Spence et al., 2006). It is also known that the B centromere size and structure can affect the transmission of B chromosome derivatives (Kaszas and Birchler 1998). Most of the B chromosome derived minichromosomes underwent nondisjunction in the presence of normal B chromosomes. The B chromosome long arm distal region and the centromere are responsible for nondisjunction of B chromosomes (Carlson 1978). For example, in the presence of normal B chromosomes, male parents transmitted 2 copies of mini-chromosomes to the progeny (Table 3). This property of B type mini-chromosomes provides a mechanism to create a dosage series of the mini-chromosomes for increased expression of genes of interest.

TABLE 3

B minichromosome sizes and transmission rates.

| Events | 76-15a | 86-74 | 86B23 | 86B155 | R2 |
|---|---|---|---|---|---|
| Chromosome Size | ½ B | ⅕ B | 1/20 B | ¾ B | NM |
| Transgene Location | distal | distal | distal | distal | distal |
| Cross | as male | as male | as male | self | self |
| Transmission | 14/36 | 3/25 | 7/29 | 9/18 | 15/46 |
| Transmission** | 30/36 | 6/25 | 8/29 | 16/18 | 16/46 |

NM indicates not measured.
*Number of progeny with minichromosomes/number of progeny tested.
** Number of minichromosomes transmitted/number of progeny tested.

Histochemical GUS Assay in Individuals of Transgenes on B Chromosomes and Derivatives As with supernumerary B chromosomes from other organisms, the B chromosome of maize is inert without any detected active genes (Jones, 1995). However, it is not known whether the lack of gene activity on B chromosomes is caused by the absence of genes or because of suppression of gene transcription by the B chromosome due to its heterochromatic nature. The transformation of the B chromosome in maize is used to determine whether there is suppression of transgene expression. In this study 17 transgenic events were recorded that had only transgenes on B chromosomes. This indicated that they were probably supported by the transgenic bar gene expression from B chromosomes, although it was possible that transgenes on A chromosomes were present but were too small to be detected by the FISH method. GUS gene expression from 9 of these events were determined by assaying the resistant calli. The absence of GUS expression from other events can be attributed to either the silencing of the GUS gene or the absence of an intact GUS gene cassette during the transformation process. However, in at least 6 events, the GUS gene expression was attributed to the transgenes on B chromosome or derivatives (Table 4). In these cases, primary roots germinated from segregating progeny were tested for GUS expression. For example, in the progeny of 76-15a, 76-15b and 86-74 outcrossed to recipient strain plants, all progeny that had transgenes on the B chromosome or truncated derivatives (14, 11 and 3 individuals, respectively) expressed GUS, but none of them that did not have transgenes on the B chromosomes or derivatives (22, 19 and 22 individuals, respectively) expressed GUS. In progeny of self pollinated 86B23 that had the smallest mini-chromosome, 23 out of 25 individuals that had transgenes on the mini-chromosomes expressed GUS, but none of the 26 that did not have the mini-chromosome showed GUS expression. The absence of GUS expression from progeny lacking the transgenes on the B chromosome and derivatives demonstrated that the GUS expression was from the transgenes on the B chromosome or derivatives and not undetected A-chromosome events. Thus transgenes inserted into the B chromosomes were expressed, at least in those sites that were tested. These sites seem to be randomly distributed along the B chromosome from the centromere to the end of the long arm of the B chromosome.

TABLE 4

Transgene expression in B minichromosomes.

| Events | 76-15a | 76-15b | 86-74 | 86B23 | 86B155 | 76-10 | 86-14 |
|---|---|---|---|---|---|---|---|
| Chromosome Size | ½ B | 1 B | ⅕ B | 1/20 B | ¾ B | 1 B | 1 B |

TABLE 4-continued

Transgene expression in B minichromosomes.

| Events | 76-15a | 76-15b | 86-74 | 86B23 | 86B155 | 76-10 | 86-14 |
|---|---|---|---|---|---|---|---|
| Transgene Location | distal | internal | distal | distal | distal | distal | centromere |
| GUS+ | 14 | 11 | 3 | 23 | 7 | 2 | 16 |
| Total | 14 | 11 | 3 | 25 | 9 | 12 | 23 |
| % | 100.0 | 100.0 | 100.0 | 92.0 | 77.8 | 16.7 | 69.6 |

Histochemical assay of GUS gene expression was performed according to Jefferson et al. (1987) by a GUS staining kit (Sigma, St. Louis, Mo.). Calli or cut roots of 2 to 5 mm long were placed directly into a 50 µl GUS staining solution arrayed in a 96 well PCR plate. The plate was wrapped with PARAFILM and incubated at 37° C. for 1 hour.

Recombination Between J11-9 and R2

To demonstrate the use of mini-chromosomes as an AC platform, the lox site on the R2 mini-chromosome was tested for Cre catalyzed exchange. A transgenic plant J11-9 with a distal transgene 35S-lox66-Cre expression cassette was crossed as a female by R2, which contains a promoterless lox71-DsRed (Clontech, Mountain View, Calif.) gene. Lox66 and lox71 are mutated lox recombination sites that can recombine most favorably in the forward reaction, as described above. Successful recombination of the two transgenes results in the exchange of the distal regions of the two transgenes and the addition of genetic material to the R2 mini-chromosome from J11-9. The recombination can be monitored by the reciprocal reaction that places the promoterless DsRed gene under the control of 35S promoter, thus producing a recognizable red fluorescence protein. The recombination events were screened on primary roots of germinated seedlings using a fluorescence stereo microscope with a Texas red filter. Four plants were identified based on the fluorescence assay from a total of 44 F1 progeny from a cross of heterozygous J11-9 by heterozygous R2. Approximately 8.7% of the progeny (about 4 plants) should have both of the transgenes based on the transmission of R2 (Table 4) and J11-9.

To determine whether the red fluorescence was a result of site-specific recombination, genomic DNA was isolated from each of the 4 plants that expressed red fluorescence, and was used as templates for PCR amplification across both of the predicted recombination products. The amplified products were sequenced and recombination at the lox site was confirmed in each case. The configurations of the sequenced regions matched the expected patterns. Thus, this minichromosome was demonstrated to be amenable for genetic manipulations via a site-specific recombination system, and can serve as a prototype of minichromosome based artificial chromosomes (ACs).

References

The references listed below are incorporated herein by reference to the extent that they supplement, explain, provide a background for, or teach methodology, techniques, and/or compositions employed herein.
U.S. Pat. No. 3,710,511
U.S. Pat. No. 3,861,709
U.S. Pat. No. 4,654,465
U.S. Pat. No. 4,727,219
U.S. Pat. No. 4,769,061

U.S. Pat. No. 4,810,648
U.S. Pat. No. 4,940,835
U.S. Pat. No. 4,959,317
U.S. Pat. No. 4,975,374
U.S. Pat. No. 5,270,201
U.S. Pat. No. 5,322,789
U.S. Pat. No. 5,445,961
U.S. Pat. No. 6,262,341
U.S. Pat. No. 5,445,961
U.S. Pat. No. 5,527,695
U.S. Pat. No. 5,530,191
U.S. Pat. No. 5,538,880
U.S. Pat. No. 5,550,318
U.S. Pat. No. 5,625,132
U.S. Pat. No. 5,658,772
U.S. Pat. No. 5,684,242
U.S. Pat. No. 5,689,041
U.S. Pat. No. 5,733,744
U.S. Pat. No. 5,736,369.
U.S. Pat. No. 5,741,684
U.S. Pat. No. 5,929,301
U.S. Pat. No. 6,175,058
U.S. Pat. No. 6,187,994
U.S. Pat. No. 7,015,372
Abe et al., *J. Biol. Chem.*, 262:16793, 1987.
Abremski et al., *Cell*, 32(4):1301-1311, 1983.
Albert et al., *Plant J.*, 7(4):649-659, 1995.
Albert et al., *Plant J.*, 7:649-659, 1995.
Alfenito and Birchler, *Genetics*, 135:589-597, 1993.
Ananiev et al., *Proc Natl Acad Sci USA*, 95:13073, 1998.
Araki et al., *J. Mol. Biol.*, 225(1):25-37, 1992.
Araki et al., *Nucleic Acids Res.*, 25(4):868-872, 1997.
Armstrong and Green, *Planta*, 164:207-214, 1985.
Arondel et al., *Science*, 258(5086):1353-1355, 1992.
Barnett et al., *Nucleic Acids Res.*, 21:27-36, 1993.
Beachy et al., *Ann. Rev. Phytopathol.*, 28:451, 1990.
Brock and Pryor, *Chromosoma*, 104:575-584, 1996.
Chang, In *Plant Breeding in the 1990s*, Stalker and Murphy (Eds.), Wallingford, U.K., CAB International, 17-35, 1992.
Chase and Gabay-Laughnan, In *Molecular Biology and Biotechnology of Plant Organelles*, Daniell and Chase, (Eds.), pp. 593-621, 2004.
Christensen et al., *Plant Molecular Biology*, 18:675-689, 1992.
Choi et al., *Nucleic Acids Res.*, 28(7):E19, 2000.
Christensen and Quail, *Transgenic Res.*, 5:213-218, 1996.
Chu et al., *Sci. Sin.*, 18:659, 1975.
Conger et al., *Plant Cell Reports*, 6:345-347, 1987.
Cox, *Proc. Natl. Acad. Sci. USA*, 80(14):4223-4227 1983.
Craig, *Ann. Rev. Genetics*, 22:77-105, 1988.
Dale and Ow, *Proc. Natl. Acad. Sci. USA*, 88(23):10558-10562, 1991.
Day et al., *Genes Dev.*, 14(22):2869-2880, 2000.
DeGreef et al., *Bio/Technology*, 7:61, 1989.
Duncan et al., *Planta*, 165:322-332, 1985.
Duvick, *Adv. Genet.* 13:1-56, 1965.
Elliot et al., *Plant Molec. Biol.*, 21:515, 1993.
Enomoto, et al., *J. Bacteriol.*, 6(2):663-668, 1983.
European Appln. 0 160 390
European Appln. 0 242 246
European Appln. 0 333 033
European Appln. 0 616 644
European Appln. 1 035 208
Farr et al., *Embo J.*, 14:5444-5454, 1995.
Farr et al., *Nat. Genet.*, 2:275-282, 1992.
Farr et al., *Proc. Natl. Acad. Sci. USA*, 88:7006-7010, 1991.

Fisher et al., *Plant Physiol.*, 102(3):1045-1046, 1993.
Fox et al. *Proc. Natl. Acad. Sci. USA*, 90(6):2486-2490, 1993.
Frame et al., *Dev. Biol.-Plant*, 36:21-29, 2000.
Frame et al., *Plant Physiol.*, 129:13-22, 2002.
Fukushige and Sauer, *Proc. Natl. Acad. Sci. USA*, 89(17):7905-7909 1992.
Futcher, *Yeast*, 4(1):27-40, 1988.
Gabay-Laughnan et al., *Genetics*, 166:959-970, 2004.
Gao et al., *Acta Botanica Sinica*, 41, 1999.
Geiser et al., *Gene*, 48:109, 1986.
Gleen et al., *Plant Molec. Biology*, 18:1185-1187, 1992.
Golic and Lindquist, *Cell*, 59(3):499-509, 1989.
Golic, *Genetics*, 137(2):551-563, 1994.
Gordon-Kamm et al., *The Plant Cell*, 2:603-618, 1990.
Green and Rhodes, *Maize for Biological Research*, 367-372, 1982.
Hamilton et al., *Proc. Natl. Acad. Sci. USA*, 93:9975-9979, 1996.
Hamilton, *Gene*, 200:107-116 1997.
Hammock et al., *Nature*, 344:458-461, 1990.
Hayes et al., *Biochem. J.*, 285(Pt 1):173-180, 1992.
Heller et al., *Proc. Natl. Acad. Sci. USA*, 93:7125-7130, 1996.
Hoess et al., *Nucleic Acids Res.*, 14(5):2287-2300, 1986.
Hoess et al., *Proc. Natl. Acad. Sci. USA*, 79:3398, 1982.
Huang et al., *J. Bacteriol.*, 179(19):6076-6083, 1997.
Huang et al., *Proc. Natl. Acad. Sci. USA*, 88:5292-5296, 1991.
Huub et al., *Plant Molec. Biol.*, 21:985, 1993.
Ito et al., *Nuc. Acid Res.* 10:1755. 1982.
Itzhaki et al., *Nat. Genet.*, 2:283-287, 1992.
Jefferson et al., *EMBO J.*, 6:3901, 1987.
Jiang et al., *Trends in Plant Sci.*, 8:570-575, 2003
Jones and Rees, B Chromosomes, Academic Press, NY, 1982.
Jones et al., *Science*, 266:7891, 1994.
Jones, *New Phytol.*, 131:411, 1995.
Kaszas and Birchler, *Genetics*, 150:1683, 1998.
Kato et al., *Proc. Natl. Acad. Sci. USA*, 101:13554-13559, 2004.
Kato et al., *Cytogenet Genome Res*, 109:156-165, 2005.
Kato and Birchler, *J. Hered.*, 97:39-44, 2006.
Kirihara et al., *Gene*, 71(2):359-370, 1988.
Knutzon et al., *Proc. Natl. Acad. Sci. USA*, 89(7):2624-2628, 1992.
Langer et al., *Nucleic Acids Res.*, 30(14):3067-3077, 2002.
Lee and Saito, *Gene*, 216(1):55-65, 1988.
Lee et al., *EMBO J.*, 7(5):1241-1248, 1988.
Liu et al., *Proc. Natl. Acad. Sci. USA*, 96:6535-6540, 1999.
Logemann et al., *Bio/technology*, 10:305, 1992.
Maeser and Kahmann, *Mol. Gen. Genet.*, 230(1-2):170-176, 1991.
Mariani et al., *Nature*, 347:737-741, 1990.
Mariani et al., *Nature*, 357:384-387, 1992.
Marshall et al., *Theor. App. Genet.*, 83:435, 1992.
Martin et al., *Science*, 262:1432, 1993.
McClintock, *Genetics*, 23:215-376, 1938.
McDonough et al., *J. Biol. Chem.*, 267(9):5931-5936, 1992.
Medberry, et al., *Nucleic Acids Res.*, 23(3):485-490, 1995.
Meyer-Leon et al., Cold Spring Harb. Symp. Quant. Biol., 49:797-804, 1984.
Mild et al., *Theor. App. Genet.*, 80:449, 1990.
Mills et al., *Hum. Mol. Genet.*, 8:751-761, 1999.
Mindrinos et al., *Cell*, 23; 78(6):1089-1099, 1994.
Murray and Szostak, *Nature*, 305:189-193, 1983.
Murray and Szostak, *Mol Cell Biol*, 6:3166-3172, 1986.
Nasuda et al., *Proc Natl Acad Sci USA*, 102:9842-9847, 2005.
O'Gorman et al., *Science*, 251(4999):1351-1355, 1991.
Ogilvie et al., *Science* 214:270, 1981

Onouchi et al., *Nucleic Acids Res.*, 19(23):6373-6378, 1991.
Onouchi et al., *Mol. Gen. Genetics*, 247:653-660, 1995.
Ow, *Curr. Op. Biotech.*, 7:181-186, 1996.
Page et al., *Genetics*, 159:291-302, 2001.
Paz et al., *Euphytica*, 136:167-179, 2004.
PCT Appln. US93/06487
PCT Appln. WO 01/11058
PCT Appln. WO 01/40492
PCT Appln. WO 91/13972
Tomizuka et al., *Proc Natl Acad Sci USA*, 97: 722-727, 2000.
Van Damme et al., *Plant Molec. Biol.*, 24:25, 1994.
Van Hartingsveldt et al., *Gene*, 127:87, 1993.
Voet et al., *Genome Res*, 11:124-136, 2001.
Wallace et al., *Nuc. Acids Res.*, 28(6):1455-1464, 2000.
Yu et al., *Genome*, 49:700, 2006.
Zheng et al., *Genetics*, 153:1435-1444, 1999.
Zhong et al., *Plant Cell*, 14:2825, 2002.

SEQUENCE LISTING

<160> NUMBER OF SEQ ID NOS: 1

<210> SEQ ID NO 1
<211> LENGTH: 7
<212> TYPE: DNA
<213> ORGANISM: Arabidopsis thaliana

<400> SEQUENCE: 1 tttaggg                                                                  7

PCT Appln. WO 98/44140
PCT Appn. WO 95/06128
Pen et al., *BioTechnology*, 10:292, 1992.
Przibilla et al., *Plant Cell*, 3:169, 1991.
Raboy et al., *Maydica*, 35:383, 1990.
Rao et al., In: *Somatic Embryogenesis in Glume Callus Cultures*, Maize Genetics Cooperation Newsletter #60, 1986.
Reddy et al. *Plant Mol. Biol.*, 22(2):293-300, 1993.
Richards and Ausubel, *Cell*, 53(1):127-136, 1988.
Rieder, *Int. Rev. Cytol.*, 79:1-58, 1982.
Sadowski, *Prog. Nucleic Acid Res. Mol. Biol.*, 51:53-91, 1995.
Saffery et al., *Proc. Natl. Acad. Sci. USA*, 98:5705-5710, 2001.
Sauer and Henderson, *Proc. Natl. Acad. Sci. USA*, 85(14): 5166-5170, 1988.
Sauer, *Biotechniques*, 16(6):1086-1088, 1994.
Sauer, *Methods*, 14(4):381-392, 1998.
Sauer, *Mol. Cell. Biol.*, 7(6):2087-2096, 1987.
Schubert, *Cytogenet Cell Genet*, 93:175, 2001.
Senecoff et al., *J. Mol. Biol.*, 201(2):405-421, 1988.
Sergaard et al., *J. Biol. Chem.*, 268:22480, 1993.
Sharopova et al., *Plant Mol Biol* 48:463-81, 2002.
Shen et al., *Hum Mol Genet*, 6:1375-1382, 1997.
Shen et al., *Curr Biol*, 10:31-34, 2000.
Shinohara et al., *Chromosome Res*, 8:713-725, 2000.
Shiroza et al., *J. BacteoL.*, 170:810, 1988.
Songstad et al., *Plant Cell Reports*, 7:262-265, 1988.
Songstad et al., *In Vitro Cell Dev. Biol-Plant*, 32:179, 1996.
Spence et al., *Chromosoma*, 115:60, 2006.
Srivastava et al., *Proc. Natl. Acad. Sci. USA*, 96:11117-11121, 1999.
Stein et al., *The Plant Journal* 13:281, 1998.
Steinmetz et al., *Mol. Gen. Genet.*, 20:220, 1985.
Sumitani et al., *Biosci. Biotech. Biochem.*, 57:1243, 1993.
Tavladoraki et al., *Nature*, 366:469, 1993.
Taylor et al., Seventh Int'l Symposium on Molecular Plant-Microbe Interactions (Edinburgh, Scotland) Abstract #497, 1994.
Trinh and Morrison, *J. Immunol. Methods*, 244(1-2):185-193, 2000.
Tomizuka et al., *Nat Genet*, 16:133-143, 1997.

What is claimed is:

1. A plant minichromosome produced by telomere-mediated truncation of one or both arms of a starting plant chromosome, wherein the minichromosome comprises heterologous engineered telomere sequences and a native plant centromere and is stably transmitted during mitosis and meiosis in a plant comprising the minichromosome that is of the same species as the plant from which the starting plant chromosome was obtained.

2. The plant minichromosome of claim 1, wherein about 25% to about 99.9% of the starting plant chromosome has been truncated.

3. The plant minichromosome of claim 1, wherein the heterologous engineered telomere sequences comprise about 2 to 100 telomere repeats.

4. The plant minichromosome of claim 3, wherein the heterologous engineered telomere sequences comprise about 6 telomere repeats.

5. The plant minichromosome of claim 1, wherein the heterologous engineered telomere sequences are from *Arabidopsis*.

6. The plant minichromosome of claim 1, wherein both arms of the starting plant chromosome have been truncated.

7. The plant minichromosome of claim 1, wherein the minichromosome is from about 1 Mb to about 100 Mb in size.

8. The plant minichromosome of claim 1, wherein the starting plant chromosome is an A chromosome.

9. The plant minichromosome of claim 1, wherein the starting plant chromosome is a B chromosome.

10. The plant minichromosome of claim 1, wherein the starting plant chromosome is from a dicot.

11. The plant minichromosome of claim 10, wherein the starting plant chromosome is from a monocot.

12. The plant minichromosome of claim 11, wherein the starting plant chromosome is from maize.

13. The plant minichromosome of claim 1, further comprising a site-specific recombination site.

14. The plant minichromosome of claim 13, wherein the site-specific recombination site is an FRT or lox site.

15. The plant minichromosome of claim 1, further comprising a transgene.

16. The plant minichromosome of claim 15, wherein the transgene confers a trait selected from the group consisting of insect resistance, herbicide tolerance, altered carbohydrate metabolism, altered fatty acid metabolism, disease resistance, male fertility restoration and pest resistance.

17. A plant cell comprising the plant minichromosome of claim 1.

18. A plant comprising the plant minichromosome of claim 1.

19. The plant of claim 17, wherein the plant is maize.

20. A seed comprising the plant minichromosome of claim 1.

21. A method of producing a plant minichromosome, comprising the steps of:
(a) transforming a starting plant chromosome with a heterologous nucleic acid comprising at least two telomere repeat sequences; and
(b) allowing telomere-mediated truncation of the starting plant chromosome to occur to produce a plant minichromosome.

22. The method of claim 21, further comprising transforming the starting plant chromosome with a site-specific recombination site.

23. The method of claim 21, wherein the site-specific recombination site is an FRT or lox site.

24. The method of claim 21, wherein the telomere repeat sequences are from *Arabidopsis*.

25. The method of claim 21, wherein the heterologous nucleic acid comprises about 6 telomere repeat sequences.

26. The method of claim 21, wherein the starting plant chromosome is transformed by *Agrobacterium*-mediated transformation.

27. The method of claim 21, wherein the starting plant chromosome is transformed by DNA bombardment.

28. The method of claim 21, wherein both arms of the starting plant chromosome are truncated.

29. The method of claim 21, wherein the starting plant chromosome is an A chromosome.

30. The method of claim 21, wherein the starting plant chromosome is a B chromosome.

31. The method of claim 21, further comprising transforming the starting plant chromosome with a selected coding sequence.

32. The method of claim 21, wherein the selected coding sequence confers a trait selected from the group consisting of insect resistance, herbicide tolerance, altered carbohydrate metabolism, altered fatty acid metabolism, disease resistance, male fertility restoration and pest resistance.

33. The method of claim 21, wherein the starting plant chromosome is comprised in a plant cell.

34. The method of claim 33, wherein the plant cell comprises at least 2 B chromosome copies.

35. The plant cell of claim 17, wherein the plant minichromosome comprises a transgene.

36. The method of claim 21, wherein the starting plant A chromosome is transformed by *Agrobacterium*-mediated transformation.

37. The method of claim 21, wherein the starting plant B chromosome is transformed by microprojectile bombardment.

38. The plant minichromosome of claim 16, wherein the coding sequence conferring male fertility restoration is a Rf3 gene.

39. The method of claim 32, wherein the coding sequence conferring male fertility restoration is a Rf3 gene.

* * * * *